United States Patent
Laufer et al.

(10) Patent No.: US 7,442,713 B2
(45) Date of Patent: *Oct. 28, 2008

(54) 2-THIO-SUBSTITUTED IMIDAZOLE DERIVATIVES AND THEIR USE IN PHARMACEUTICS

(75) Inventors: Stefan Laufer, Blaubeuren (DE); Hans-Guenter Striegel, Blaustein (DE); Wolfgang Albrecht, Ulm (DE); Karola Tollmann, Brechen (DE)

(73) Assignee: Merckle GmbH, Ulm (DE)

( * ) Notice: Subject to any disclaimer, the term of this patent is extended or adjusted under 35 U.S.C. 154(b) by 456 days.

This patent is subject to a terminal disclaimer.

(21) Appl. No.: 10/514,911

(22) PCT Filed: May 16, 2003

(86) PCT No.: PCT/EP03/05172

§ 371 (c)(1),
(2), (4) Date: May 10, 2005

(87) PCT Pub. No.: WO03/097633

PCT Pub. Date: Nov. 27, 2003

(65) Prior Publication Data

US 2006/0252810 A1 Nov. 9, 2006

(30) Foreign Application Priority Data

May 17, 2002 (DE) .................. 102 22 103

(51) Int. Cl.
*A61K 31/44* (2006.01)
*C07D 401/04* (2006.01)

(52) U.S. Cl. .............. 514/341; 548/300.1; 548/311.1; 548/314.7; 546/268.1; 546/272.7; 546/274.1; 514/336; 514/340

(58) Field of Classification Search .......... 546/268.1, 546/272.7, 274.1; 548/311.1, 314.7; 514/336, 514/340, 341

See application file for complete search history.

(56) References Cited

U.S. PATENT DOCUMENTS 6,300,347 B1 * 10/2001 Revesz ............. 514/333
6,432,988 B1 * 8/2002 Laufer et al. ........ 514/341
7,253,191 B2 * 8/2007 Laufer et al. ........ 514/341

FOREIGN PATENT DOCUMENTS

DE  101 07 683 A    8/2002
WO  WO 88/01167 A1  2/1988
WO  WO 99/03837 A   1/1999

OTHER PUBLICATIONS

Laufer et al., "Towards the Improvement of the Synthesis of Novvel 4(5)-aryl-5(4)-heteroaryl-2-thio-substituted Imidazoles and Their p38 MAP Kinase Inhibitory Activity" J. Royal Soc. Chem. 6:437-439, 2008.

* cited by examiner

*Primary Examiner*—Golam M Shameem
(74) *Attorney, Agent, or Firm*—Rothwell, Figg, Ernst & Manbeck, P.C.

(57) ABSTRACT

The invention relates to 2-thio-substituted imidazole derivatives of the formula I

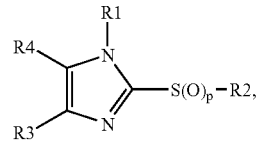

in which the radicals $R_1$, $R_2$, $R_3$, $R_4$ and p are as defined in the description. The compounds according to the invention have immunomodulating and/or cytokine-release-inhibiting action and are therefore suitable for treating disorders associated with a disturbed immune system.

14 Claims, No Drawings

2-THIO-SUBSTITUTED IMIDAZOLE DERIVATIVES AND THEIR USE IN PHARMACEUTICS

CROSS-REFERENCE TO RELATED APPLICATION

This application is a National Phase of International Application Serial No. PCT/EP03/005172, filed May 16, 2003.

FIELD OF THE INVENTION

The present invention relates to 2-thio-substituted imidazole derivatives having immunomodulating and cytokine-release-inhibiting action, to pharmaceutical compositions comprising these compounds and to their use in pharmacy.

DESCRIPTION OF THE BACKGROUND ART

Pharmacologically active imidazole compounds with antiinflammatory activity are already known.

Thus, inter alia, compounds having 4,5-di(hetero)arylimidazole moieties have been examined more closely, and various pharmaceutical actions thereof have been described. Also known are compounds which are substituted in the 2-position. U.S. Pat. No. 4,585,771 discloses 4,5-diphenylimidazole derivatives which are substituted in the 2-position by a pyrrolyl, indolyl, imidazolyl or thiazolyl radical and which have antiinflammatory and antiallergic activity.

U.S. Pat. Nos. 4,528,298 and 4,402,960 describe 4,5-di(hetero)arylimidazole derivatives which are substituted in the 2-position via a thio, sulfinyl or sulfonyl group by a phenyl, pyridyl, N-oxypyridyl, pyrimidyl, thiazolyl or thienyl radical and which have antiinflammatory and antiallergic activity.

U.S. Pat. Nos. 4,461,770, 4,608,382 and 4,584,310 describe 4-(5-aryl)-5-(4-heteroaryl)imidazole derivatives which are substituted in the 2-position via a thio, sulfinyl or sulfonyl group by a substituted or unsubstituted aliphatic hydrocarbon and which, inter alia, have antiinflammatory action.

WO 00/17192 relates to 4-heteroaryl-5-phenylimidazole derivatives which are substituted in the 2-position by a phenylalkylthio group. These compounds act as antiinflammatories and inhibitors of cytokine release. WO 99/03837 and WO 93/14081 describe 2-substituted imidazoles which inhibit the synthesis of a number of inflammatory cytokines. The compounds described in WO 93/14081 have in the 2-position, attached via a sulfur atom, a phosphorus-containing substituent or an aryl or heteroaryl substituent. WO 91/10662 describes imidazole derivatives which inhibit the acyl-CoA: cholesterol 0-acyl transferase and binding of thromboxane $TxA_2$. WO 95/00501 describes imidazole derivatives which can be used as cyclooxygenase inhibitors. The imidazole derivatives described in U.S. Pat. Nos. 4,440,776; 4,355,039 and 4,269,847 have antiinflammatory, antiallergic and immunostimulating action. DE 35 04 678 describes imidazole derivatives which can be used for treating atherosclerotic, thromboembolic and inflammatory diseases and diseases which are associated with lipid metabolism. GB 1 564 184 describes 2-polyfluoro-$C_1$-$C_2$-alkyl-substituted imidazole compounds having anti-inflammatory action. WO 96/03387 and WO 02/066485, too, describe substituted imidazole compounds having anti-inflammatory action.

J. Med. Chem. 1996, 39, 3927-37 describes compounds having 5-lipoxygenase- and cyclooxygenase-inhibiting action, 2-(4-methylsulfinylphenyl)-4-(4-fluorophenyl-5-(pyrid-4-yl)imidazole also having cytokine-inhibiting action. Further 2-thio-substituted imidazole derivatives are described in EP 372 445, U.S. Pat. No. 4,190,666, GB 1 155 580, JP 01-040 467, Acta Chim. 1969, 61, 69-77 and J. prakt. Chem. 1972, 314, 785-792.

It has been found that the known compounds are unstable and difficult to process, or that their efficacy is low.

In spite of the fact that numerous compounds are known, there is therefore still a need for compounds having antiinflammatory action which inhibit cytokine release.

SUMMARY OF THE INVENTION

It is an object of the invention to provide such compounds.

Surprisingly, it has now been found that certain 2-substituted imidazole derivatives represent stable compounds which are readily processible and which have high immunomodulating and/or cytokine-release-inhibiting activity.

Accordingly, the present invention provides
2-thio-substituted imidazole derivatives of the formula I

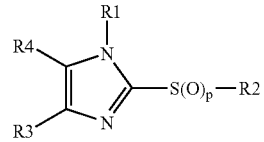

in which $R^1$, $R^2$, $R^3$, $R^4$ and n are as defined below:

$R^1$ is H or $C_1$-$C_6$-alkyl, $R^2$ is selected from the group consisting of:

a) C1-C6-Alkyl which is substituted by 1, 2 or 3 hydroxyl groups, halogen atoms, NR5R6 or C1-C4-alkoxy groups, where R5 is H, C1-C6-alkyl, phenyl-C1-C6-alkyl or phenyl and R6 is H, C1-C6-alkyl. Here, the hydroxyl groups, the substituted or unsubstituted amino groups and the alkoxy groups are located on different carbon atoms of the alkyl group. Preferably, the alkyl group is substituted by 2 or 3 hydroxyl groups, and particularly preferably, the alkyl group has 2 or 3 carbon atoms. A preferred example of such a radical is a radical of the formula —CH2-CHOH—CH2OH.

b) C1-C6-Alkyl which is substituted by 1, 2 or 3 radicals of the formula —COOR5, where R5 is H, C1-C6-alkyl, phenyl-C1-C4-alkyl or phenyl. The radical —COOR5 is preferably located at the terminal carbon atom of the alkyl group. Preferred examples of such radicals are:

—(CH$_2$)$_n$—CH(COOR$^5$)$_2$, where n is 0, 1, 2 or 3,

—(CH2)n-COOR5, where n is 1, 2, 3 or 4.

c) C1-C6-Alkyl which is substituted by at least one radical of the formula —COOR5 and at least one hydroxyl group, where R5 is H, C1-C6-alkyl, phenyl-C1-C4-alkyl or phenyl. Preferably, the radical —COOR5 is located at the carbon atom of the alkyl group which is attached to the sulfur atom and the hydroxyl group at the terminal carbon atom of the alkyl group.

DETAILED DESCRIPTION OF THE PREFERRED EMDOBIMENTS

A preferred radical of this type is —CH(COOH)—(CH2)n-OH, where n is 1, 2 or 3.

d) A radical of the formula II

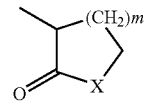

in which X is O or $NR^6$, m is 1 or 2 and $R^6$ is H or $C_1$-$C_6$-alkyl.

e) $C_1$-$C_6$-Alkyl which is substituted by a radical of the formula III or IV

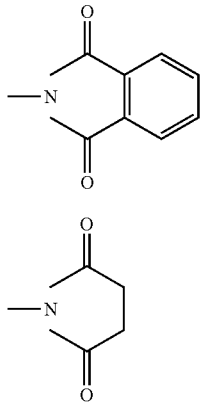

f) A radical of the formula

—(CH2)n-CO—R7 in which $R^7$ is $C_1$-$C_3$-alkyl, phenyl, benzyl or phenethyl and n is 1, 2 or 3. A preferred radical of this type is the acetonyl radical —$CH_2COCH_3$.

g) A radical of the formula

—(CH2)n-CO—CH2-CO—R7 in which R7 is C1-C3-alkyl, phenyl, benzyl or phenethyl and n is 1, 2 or 3. A preferred radical of this formula is the radical —CH2-COCH2COCH3.

h) A radical of the formula

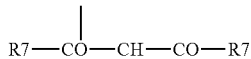

in which the radicals R7, which are identical or different, are C1-C3-alkyl, phenyl, benzyl or phenethyl. A preferred radical is —CH(COCH3)2.

i) A radical of the formulae

—(CH2)n-CO—CHOH—R7

—(CH2)n-CHOH—CO—R7

—(CH2)n-CO—CH2-CHOH—R7

—(CH2)n-CHOH—CH2-CO—R7 in which R7 is C1-C3-alkyl, phenyl, benzyl or phenethyl and n is 1, 2 or 3.

j) A radical of the formulae

—(CH2)n-CO—CH2-COOR5

—CH(COR7)-COOR5

—(CH2)n-COCOOR5 in which R5 is H, C1-C6-alkyl, phenyl-C1-C4-alkyl or phenyl, R7 is C1-C3-alkyl, phenyl, benzyl or phenethyl and n is 1, 2 or 3.

Preferred radicals of this type are —CH2COCH2COOR5, —CH2COCOOR5 and —CH(COCH3)-COOR5, where R5 is C1-C4-alkyl.

k) A radical of the formula

—$(CH_2)_n$—$CONR^8R^9$ in which $R^8$ and $R^9$, which may be identical or different, are H, $C_1$-$C_6$-alkyl, $C_1$-$C_6$-alkyl which is substituted by one, two or three hydroxyl groups, $C_1$-$C_6$-alkyl which is substituted by a COOH group, phenyl or benzyl, or $R^8$ and $R^9$ together with the nitrogen atom to which they are attached are a saturated heterocycle which has 5 or 6 ring atoms and one or two heteroatoms independently of one another selected from the group consisting of N, O and S, and n is 1, 2 or 3, and which may be substituted by one or two groups independently of one another selected from the group consisting of $C_1$-$C_6$-alkyl and hydroxyl.

Preferably, one of the radicals $R^8$ and $R^9$ is H. Preference is furthermore given to radicals of the above formula in which one of the radicals $R^8$ and $R^9$ is H and the other is $C_1$-$C_6$-alkyl, piperidinyl or morpholinyl and in particular $C_1$-$C_6$-alkyl which is substituted by 1, 2 or 3 hydroxyl groups (at different carbon atoms). Preference is furthermore given to compounds of the above formula in which $R^8$ and $R^9$ are $C_1$-$C_6$-alkyl which is substituted by 1, 2 or 3 hydroxyl groups.

Other preferred groups —$(CH_2)_n CONR^8R^9$ are:

—$(CH_2)_n CONHCH_2CHOHCH_2OH$

—$(CH_2)_n CONHCH_2CO_2H$

—$(CH_2)_n CON(CH_2CH_2OH)_2$

—$(CH_2)_n CONHC(CH_3)(CH_2CH_2OH)_2$

—$(CH_2)_n CONHC(CH_2OH)_3$ where n is 1, 2 or 3. —$(CH_2)_n CON(CH_2CH_2OH)_2$ is particularly preferred.

If $R^8$ and $R^9$ together are a heterocycle, this is preferably morpholino, piperidino or piperidino which is substituted at one of the carbon atoms by one or two OH groups.

l) A radical of the formula

—$(CH_2)_n CONR^{10}$—$CONR^8R^9$ in which $R^8$ and $R^9$ have the meanings give above under k) and $R^{10}$ is H or $C_1$-$C_6$-alkyl.

Preferably, $R^8$ and $R^{10}$ are H and $R^9$ is H, $C_1$-$C_6$-alkyl, benzyl or phenyl.

m) C2-C6-Alkenyl which is substituted by one or two groups of the formula —COOR5, where R5 is H, C1-C6-alkyl, phenyl or benzyl. This is preferably a radical of the formula —(CH2)n-CH=CH—COOR5 in which R5 is H or C1-C6-alkyl and n is 1, 2 or 3.

n) C1-C6-Alkyl which is substituted by a non-aromatic 3- to 6-membered heterocyclic radical which has one or two heteroatoms independently of one another selected from the group consisting of N and O. This is preferably an oxazolidine radical, in particular an oxazolidin-2-one radical, or an oxiranyl radical. The oxazolidine radical is preferably attached via the 4-position to the alkyl group.

p is 0, 1 or 2;

one of the radicals R3 and R4 is 4-pyridyl which may have 1 or 2 substituents independently of one another selected from the group consisting of amino, C1-C4-alkylamino, di-C1-C4-alkylamino, phenyl-C1-C4-alkylamino and —NR12COR11, where R11 is C1-C4-alkyl, phenyl which may have one or two substituents independently of one another selected from the group consisting of C1-C4-alkyl, C1-C4-alkoxy and halogen, and R12 is H, C1-C4-alkyl or benzyl, and the second of the radicals R3 and R4 is aryl which is optionally substituted by a halogen atom.

The invention also provides the optical isomers and physiologically acceptable salts of the compounds of the formula I.

If the compounds according to the invention have centers of asymmetry, the scope of the invention includes both racemates and optical isomers (enantiomers, diastereomers).

The term "alkyl" (also in combination with other groups, such as phenylalkyl, etc.) embraces straight-chain and branched alkyl groups having preferably 1 to 6 or 1 to 4 carbon atoms, such as methyl, ethyl, n- and i-propyl, n-, i- and t-butyl, sec-butyl, n-pentyl and n-hexyl.

The term "aryl" embraces aromatic ring systems, such as phenyl or naphthyl.

The term "halogen" represents a fluorine, chlorine, bromine or iodine atom, in particular a fluorine or chlorine atom.

C3-C6-Cycloalkyl groups are cyclopropyl, cyclobutyl and, in particular, cyclopentyl and cyclohexyl.

Nonaromatic heterocyclic radicals can be saturated or unsaturated. Preference is given to piperidinyl, piperazinyl, pyranyl, morpholinyl or pyrrolidinyl, where the piperidinyl radical may be substituted by 1, 2, 3 or 4 C1-C4-alkyl groups, in particular methyl groups.

Preferred aromatic heterocyclic radicals are 2-, 3- or 4-pyridyl, pyrimidinyl, pyrrolyl, imidazolyl, oxazolyl, isoxazolyl, furyl, thienyl or thiazolyl. The heterocyclic radical, in particular the pyridyl radical, may be substituted as mentioned above. The pyridyl radical is substituted in particular in the 2-position.

Phenyl-C1-C4-alkyl is in particular benzyl or phenylethyl.

Preference is given to compounds of the formula I in which R3 is 4-halogen-substituted phenyl and $R^4$ is 4-pyridyl.

According to a particularly preferred embodiment, the radical R3 in the formula I is 4-fluorophenyl and R4 is 4-pyridyl or substituted 4-pyridyl, where phenyl-C1-C6-alkylamino and —NR12COR11 are particularly preferred substituents.

R11 is preferably C1-C6-alkyl. R12 is preferably H or C1-C6-alkyl.

Particular preference is given to compounds of the formula in which R4 is 4-pyridyl, which is substituted by amino, C1-C4-alkylamino or NR11 COR12, R1 is C1-C3-alkyl and R2 is C1-C3-alkyl which is substituted by one or two hydroxyl groups, one or two groups COOR5 or one or two groups —(CH2)nconr8r9, where R5, R8, R9, R11, R12 and n are as defined above. R8 and R9, which may be identical or different, are particularly preferably H or C1-C6-alkyl which is optionally substituted by one or two hydroxyl groups.

In the present case, the physiologically acceptable salts can be acid addition salts or base addition salts. For acid addition salts, inorganic acids, such as hydrochloric acid, sulfuric acid or phosphoric acid, or organic acids, such as tartaric acid, citric acid, maleic acid, fumaric acid, malic acid, mandelic acid, ascorbic acid, gluconic acid and the like, are used.

The compounds according to the invention are prepared in a two-step process. In the first step, initially a substituted imidazole-2-thione (R2=H) is prepared. This is then reacted in the second step such that the desired substituent is introduced.

1) Preparation of the imidazole-2-thione

Two process variants are available for preparing the imidazole-2-thione. The two variants are illustrated in an exemplary manner using compounds in which R3 is 4-fluorophenyl and R4 is 4-pyridyl. Compounds having other radicals R3 and R4 can be prepared in an analogous manner.

Variant 1

The synthesis of the substituted imidazole-2-thiones is carried out according to the course of the reaction of scheme 1, using ethyl isonicotinate and 4-fluorophenyl-acetonitrile as starting materials.

The starting materials are converted in a condensation reaction with the aid of metallic sodium in an alcohol, for example ethanol, into 2-cyano-2-(4-fluorophenyl)-1-(4-pyridyl)ethanone (compound 1). The cyano group is then removed by hydrolysis, for example with hydrobromic acid, and decarboxylation, giving 2-(4-fuorophenyl)-1-(4-pyridyl) ethanone (compound 2). In the next step, compound 2 is nitrosated in the 2-position using, for example, nitrites, such as sodium nitrite or isoamyl nitrite. This gives the compound of the formula (3), the oxime 2-(4-fluorophenyl)-1-(4-pyridyl)-α-hydroxyiminoethane.

Using this intermediate, cyclization giving an imidazole derivative of the formula (4), a substituted 5-(4-fluorophenyl)-4-(4-pyridyl)imidazole N-oxide which carries the substituent R1 at the nitrogen atom in 3-position, is carried out by reaction with an imine of the general formula H2C=NR1, which is present as a 1,3,5-trisubstituted hexahydro-1,3,5-triazine, in an alcoholic solvent, such as ethanol, and at elevated temperature (50-90° C.). The imidazole N-oxide of the formula (4) is then reacted with 2,2,4,4-tetramethyl-3-thiocyclobutanone in a chlorinated solvent to give the corresponding 3-substituted 5-(4-fluorophenyl)-4-(4-pyridyl)imidazole-2-thione (compound 5; compound of the formula I where $R^2$=H).

Scheme 1:
Synthesis route for the thiones according to the invention (variant 1)

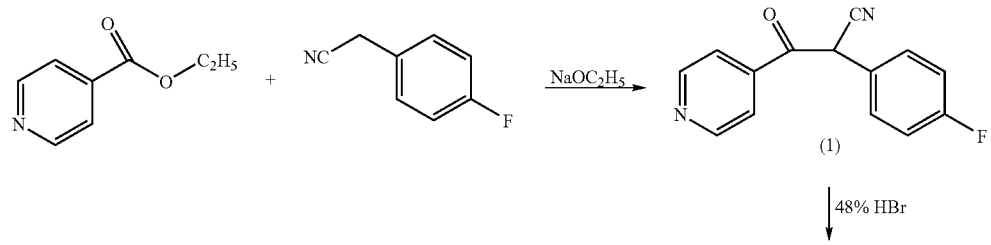

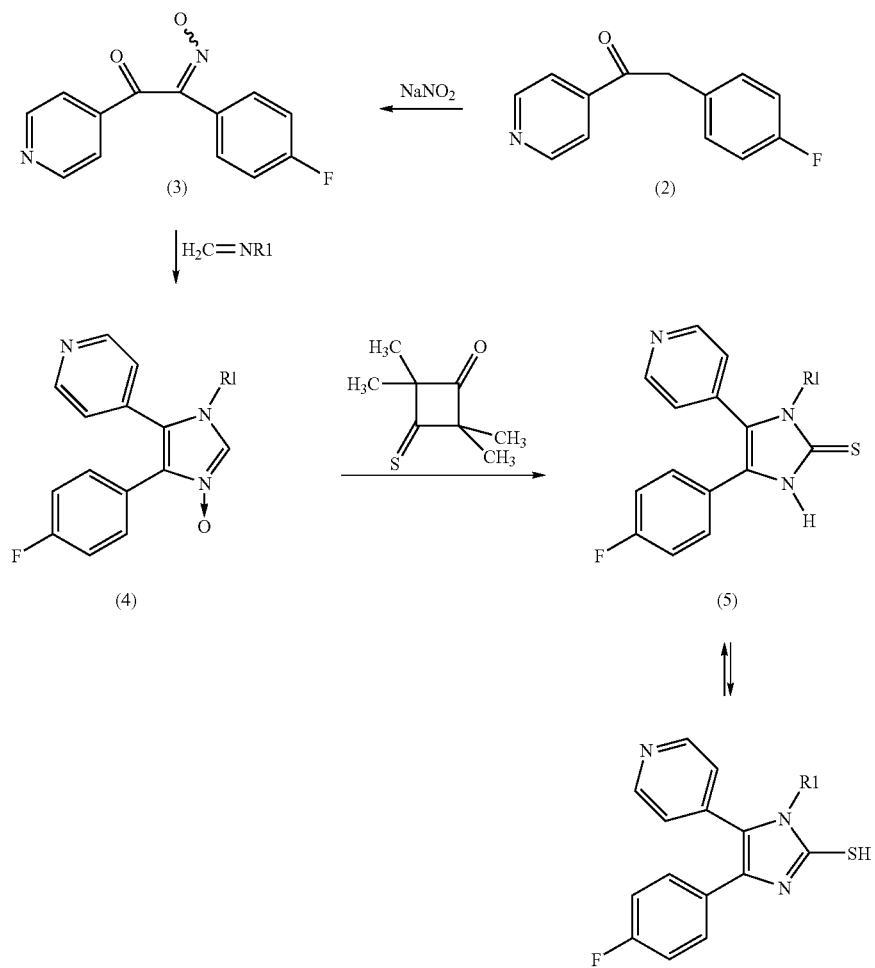
Variant 2
Initially, the oxime compound of the formula (3), 2-(4-fluorophenyl)-1-(4-pyridyl)-α-hydroxyiminoethane, is prepared as described in variant 1 (scheme 1, steps 1 to 3). Using this starting material, the synthesis of the substituted imidazole-2-thiones is carried out according to scheme 2.
Scheme 2:
Synthesis route for the thiones according to the invention (variant 2)
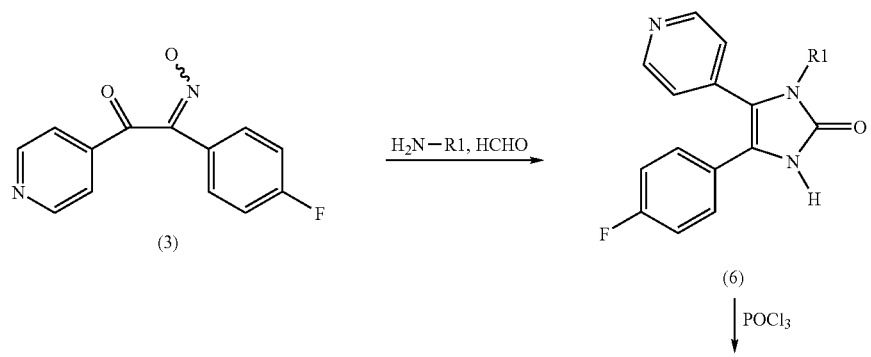

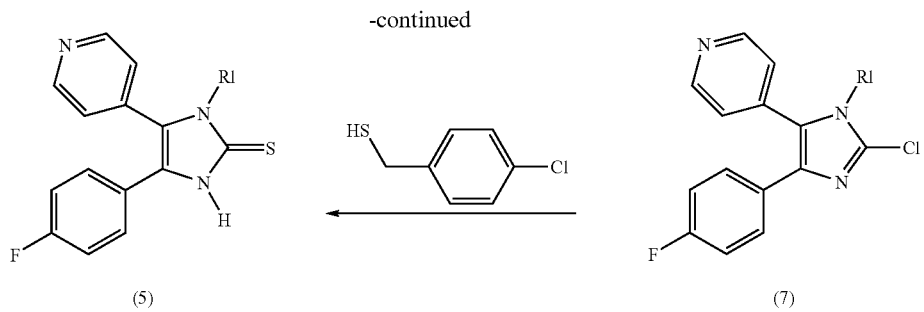

2-(4-Fluorophenyl)-1-(4-pyridyl)-α-hydroxyiminoethane is, according to scheme 2, reacted with the selected amine of the general formula NH2-R1 and formaldehyde, giving, with ring closure, a compound of the formula (6), i.e. a 1-substituted 4-(4-fluorophenyl)-5-(4-pyridyl)imidazol-2-one. This is reacted with an excess of phosphorus oxychloride, resulting in a compound of the formula (7), i.e. a 1-substituted 4-(4-fluorophenyl)-5-(4-pyridyl)imidazole 2-chloride being formed. From this compound, the corresponding 1-substituted 4-(4-fluorophenyl)-5-(4-pyridyl)imidazole-2-thione (compound 5) is obtained by reaction with 4-chlorobenzylthiol in a polar aprotic solvent and at elevated temperature (100-150° C.).

2) Preparation of the 2-thioimidazole Compound

The thione compounds (5) obtained according to variant 1 or 2 are converted by substitution of the sulfur atom in the 2-position into the compounds of the formula I according to the invention. The substitutions can be carried out in a known manner by a nucleophilic substitution reaction, as shown in an exemplary manner for some compounds in scheme 3. Here, compound 5 is reacted with R2-X in an inert polar solvent, such as an alcohol. X is a readily exchangeable group, such as Hal, in particular Cl, Br, I, methylsulfonyl, tosyl etc. Suitable processes are known to the person skilled in the art and are described, for example, in DE 198 42 833, EP 0 372 445 and U.S. Pat. No. 4,440,776. The compounds R2-X are known or can be prepared by known processes. If R2 is the abovementioned radical k) or the radical l), the compounds R2-X where X=Cl may be prepared by the process described in J. Amer. Chem. Soc. 78, 2556-2559 (1956). Compounds R2-X in which R2 has a carboxyl or ester group can be prepared by the process described in J. Heterocycl. Chem. 21, 753-757 (1984). Compounds R2-X in which R2 embraces a 1,3-dicarbonyl grouping can be prepared by the process described in J. Org. Chem. 27, 1251-1254 (1962).

The corresponding regioisomeric compounds can be prepared in accordance with scheme (4). Starting with 1-(4-fluorophenyl)-2-(4-pyridyl)-α-hydroxyiminoethanone (obtained analogously to scheme 1), compounds of the formula 15 are obtained analogously to the process of scheme 1 by reaction with the appropriate imines. Compound (13) can be prepared by the process described in WO 93/14081.

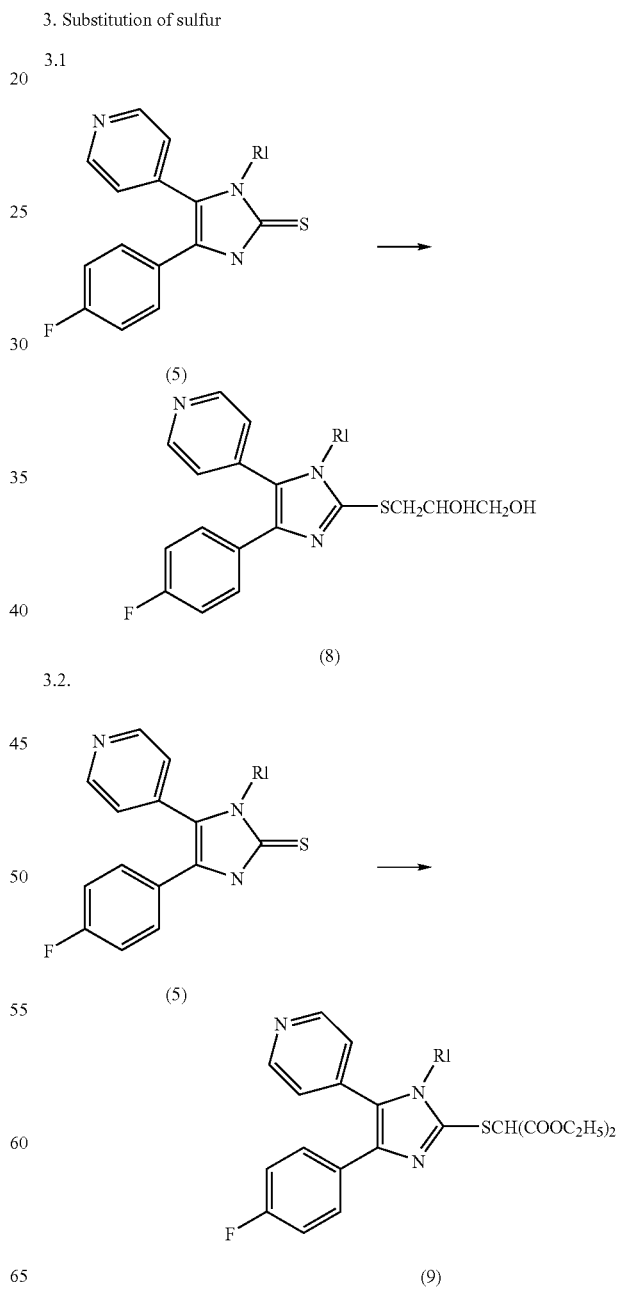

3.3.

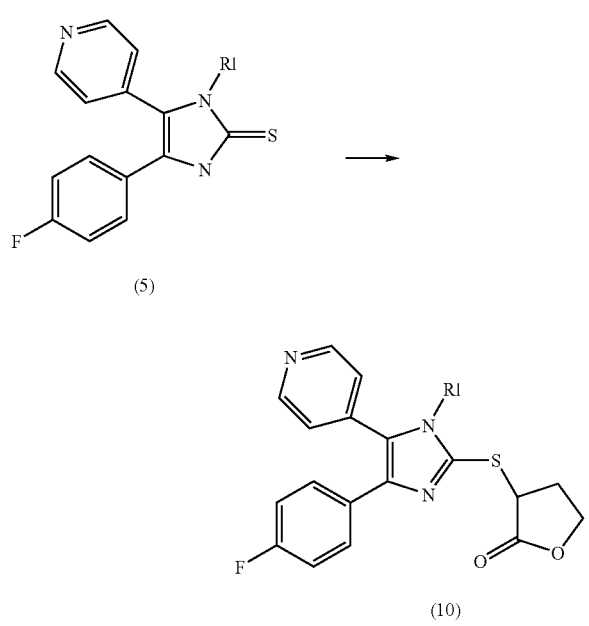

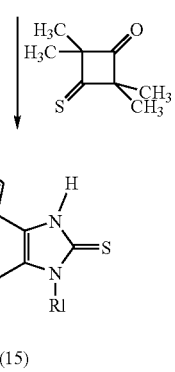

These compounds can be reacted further as described in scheme 3.

The imidazolethiols which carry a C1-C4-alkyl group in the 4-position are obtained from the corresponding α-hydroxyiminoethanones (compound 17/19 in scheme 5 below), analogously to schemes 1 and 2.

Scheme 5

4-Methylimidazolethiones 6.1.

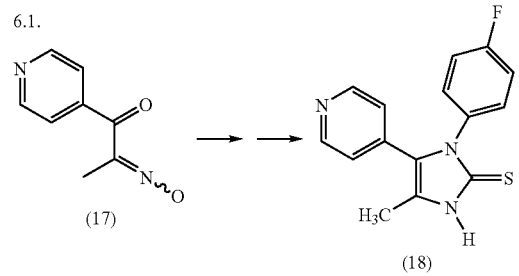

6.2.

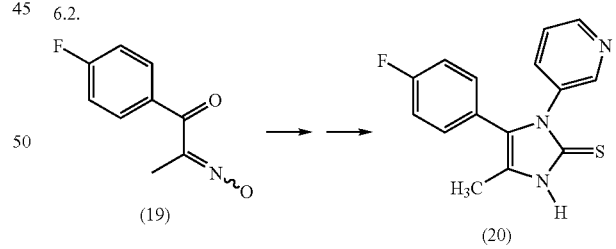

These compounds can be reacted further according to schemes 3 and 4. The corresponding regioisomeric compounds can be prepared analogously to scheme 4.

The preparation of the compounds in which $R^4$ is an amino- or amido-substituted heterocyclic radical, in particular a pyridyl radical, is carried out according to scheme 6, where the preparation is illustrated using 2-substituted 4-pyridine compounds as examples (compounds in which $R^4$ is an alkyl-substituted heterocyclic radical are prepared by the processes mentioned above using appropriately substituted starting materials):

Scheme 4

Regioisomeric thiones

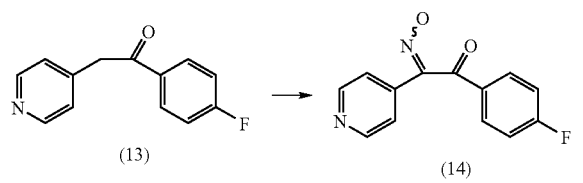

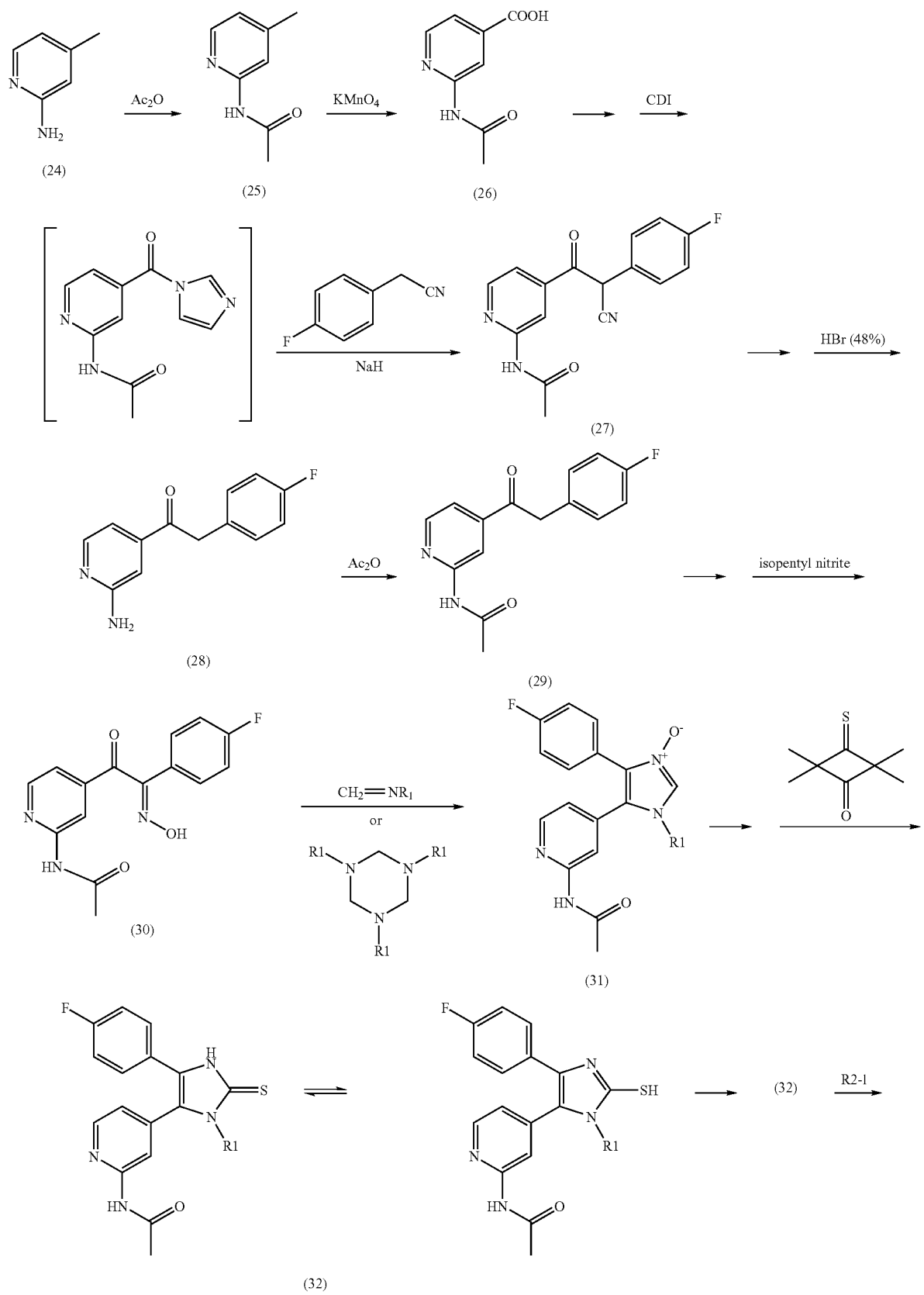

-continued

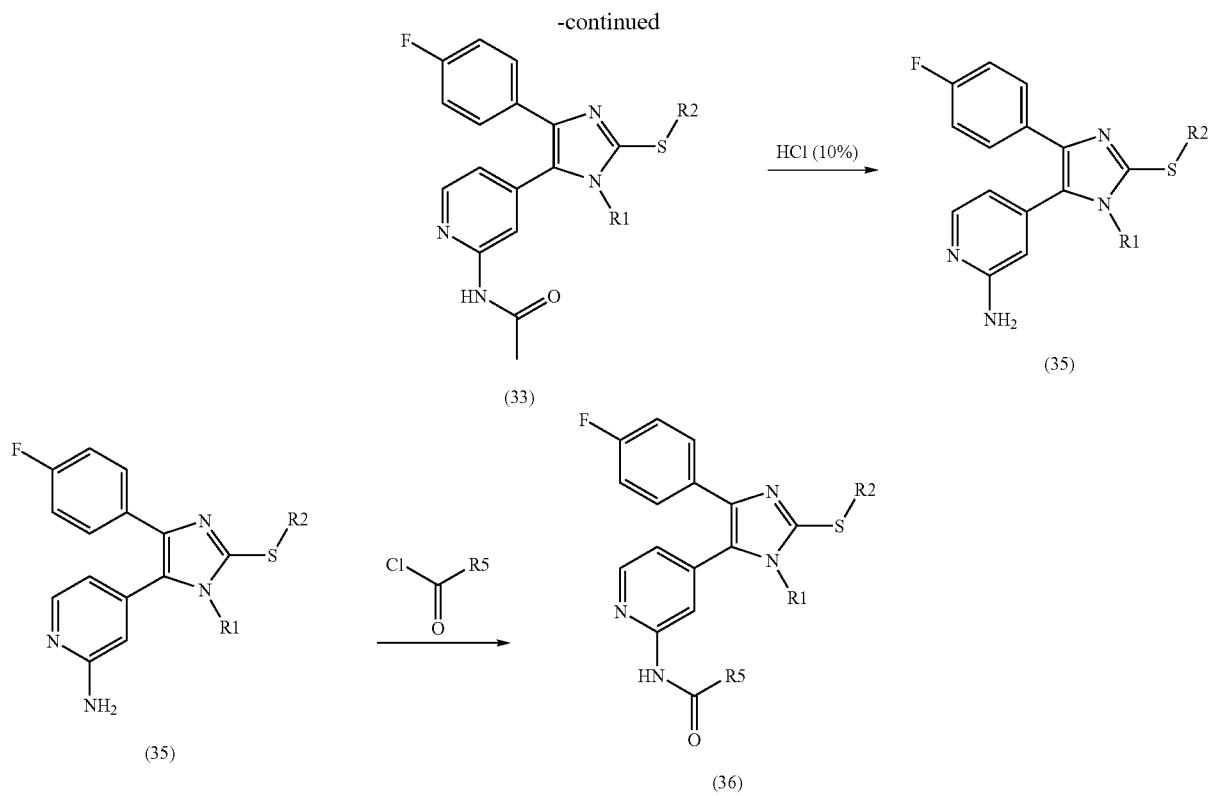

(CDI = carbonyldiimidazole)

The amino group of the starting material 2-amino-γ-picolin (24) is protected, for example by introduction of an acetyl group using acetic anhydride. The methyl group of the compound (25) is then oxidized to the carboxyl group using, for example, potassium permanganate in an aqueous medium at from 20 to 90° C.

The reaction of the resulting pyridinecarboxylic acid (26) with 4-fluorophenyl-acetonitrile to give compound (27) and the subsequent removal of the nitrile group are carried out in accordance with variant 1. This also results in the removal of the acetyl group on the amino group of the pyridine compound, with the compound (28) being formed.

In the next step, the amino group is again protected, for example by introducing an acetyl group using acetic anhydride. The resulting compound (29) is, in accordance with variant 1 or 2 (shown in scheme 6 using variant 1), converted into the thiono compound (32). Into this compound, the desired radical R2 is introduced as described in scheme 3.

To introduce the desired substituent into the pyridyl group, the acetyl group is initially removed hydrolytically, for example using aqueous acid, giving the amino compound (35). An acyl radical is introduced by acylation, in particular with the corresponding acid chloride R5COCl in an inert solvent, such as an ether, for example tetrahydrofuran or dioxane, or in a chlorinated hydrocarbon, for example methylene chloride or 1,2-dichloroethan, etc. The acylation is generally carried out in the presence of a base, for example triethylamine, in an at least equimolar amount.

To prepare the substituted amine compounds, compound (35) is reacted with one or two molar equivalents of an alkyl bromide or phenylalkyl bromide in an inert solvent, such as dimethylformamide, in the presence of a base, such as sodium hydride, to give the compounds (37) or (38). Alternatively, the amide compounds (34) or (36) can be reduced with lithium aluminum hydride, for example in tetrahydrofuran, to give compound 39.

In vitro and in vivo, the compounds according to the invention show immunomodulating and cytokine-release inhibiting action. Cytokines are proteins such as TNF-α and IL-β which play an important role in numerous inflammatory disorders. The compounds according to the invention are, owing to their cytokine-release-inhibiting action, suitable for treating disorders which are associated with a disturbance of the immune system. They are suitable, for example, for treating autoimmune disorders, cancer, rheumatoid arthritis, gout, septic shock, osteoporosis, neuropathic pain, the spread of HIV, HIV dementia, viral myocarditis, insulin-dependent diabetes, periodontal disorders, restenosis, alopecia, T-cell depletion associated with HIV infections or AIDS, psoriasis, acute pancreatitis, rejection reactions of allogenic transplants, allergic pneumonia, arteriosclerosis, multiple sclerosis, cachexia, Alzheimer's disease, stroke, ictus, colitis ulcerosa, morbus Crohn, inflammatory bowel disease (IBD), ischemia, congestive heart failure, pulmonary fibrosis, hepatitis, glioblastoma, Guillain-Barre syndrome, systemic lupus erythematodes, adult respiratory distress syndrome (ARDS) and respiratory distress syndrome.

The compounds according to the invention can be administered either as individual therapeutically active compounds or as mixtures with other therapeutically active compounds. The compounds can be administered on their own; in general, however, they are formulated and administered in the form of pharmaceutical compositions, i.e. as mixtures of the active compounds with suitable pharmaceutical carriers or diluents. The compounds or compositions can be administered orally or parenterally; preferably, they are administered in oral dosage forms.

The type of pharmaceutical composition or carrier or diluent depends on the desired administration form. Oral compositions, for example, can be present as tablets or capsules and may comprise customary excipients, such as binders (for example syrup, gum arabic, gelatin, sorbitol, tragacanth or polyvinylpyrrolidone), fillers (for example lactose, sugar, cornstarch, calcium phosphate, sorbitol or glycerol), glidants (for example magnesium stearate, talc, polyethylene glycol or silica), disintegrants (for example starch) or wetting agents (for example sodium lauryl sulfate). Liquid oral preparations can assume the form of aqueous or oily suspensions, solutions, emulsions, syrups, elixirs or sprays and the like. They can also be present as a dry powder which is reconstituted using water or another suitable carrier. Such liquid preparations may comprise customary additives, for example suspending agents, flavors, diluents or emulsifiers. For parenteral administration, it is possible to use solutions or suspensions with customary pharmaceutical carriers.

The compounds or compositions according to the invention can be administered to mammals (man or animal) in a dose of from about 0.5 mg to 100 mg per kg of body weight per day. They may be administered in one individual dose or in a plurality of doses. The activity spectrum of the compounds as inhibitors of cytokine release was examined using the test systems below, as described by C. Donat and S. Laufer in Arch. Pharm. Pharm. Med. Chem. 333, Suppl. 1, 1-40, 2000.

In vitro Test with Human Whole Blood

The test substance is added to samples of human potassium-EDTA whole blood (of 400 µl each) and the samples are preincubated in a $CO_2$ incubator (5% $CO_2$; 95% moisture-saturated air) at 37° C. for 15 min. The samples are then stimulated with 1 µg/ml of LPS (*E. coli* 026:B6) at 37° C. in a $CO_2$ incubator (5% $CO_2$; 95% moisture-saturated air) for 4 hours. The reaction is stopped by placing the samples on ice, adding DPBS buffer and then centrifuging at 1000*g for 15 min. The amount of IL-1β and TNFα in the plasma supernatant is then determined by ELISA.

In Vitro Test with PBMCs

1) The mononuclear cells (PBMCs) from human potassium-EDTA whole blood, diluted 1:3, are isolated by density gradient centrifugation (Histopaque®-1.077). The cells are washed twice with DPBS buffer, resuspended in macrophage SFM medium and adjusted to a cell count of 1*106 cells/ml.

The resulting PBMCs suspension (samples of in each case 390 µl) and the test substance are preincubated at 37° C. in a CO2 incubator (5% CO2; 95% moisture-saturated air) for 15 min. The samples are then stimulated with in each case 1 µl/ml of LPS (*E. coli* 026:B6) at 37° C. in a $CO_2$ incubator (5% $CO_2$; 95% moisture-saturated air) for 4 hours. The reaction is stopped by placing the samples on ice, adding DPBS buffer and then centrifuging at 15 880*g for 12 min. The amount of IL-1β and TNFα in the plasma supernatant is then determined by ELISA.

2) Kinase Assay

At 37° C., microtiter plates were coated with 50 µl of ATF2 solution (20 µl/ml) for one hour. The plates were washed three times with water, and 50 µl of kinase mixture (50 mM tris-HCl, 10 mM MgCl2, 10 mM β-glycerol phosphate, 10 µg/ml BSA, 1 mM DTT, 100 µM ATP, 100 µM Na3VO4, 10 ng of activated p38α) with or without inhibitor were then added into the wells, and the plates were incubated at 37° C. for 1 hour. The plates were washed three times and then incubated at 37° C. with phosphorus-ATF-2 antibodies for one hour. Once more, the plates were washed three times, and goat-anti-rabbit IgG labeled with alkaline phosphatase was then added at 37° C. for one hour (to immobilize antibody-phosphorylated protein-substrate complex). After washing three times, the alkaline phosphatase-substrate solution (3 mM 4-NPP, 50 mM NaHCO3, 50 mM MgCl2, 100 µl/well) was added at 37° C. for 1.5 hours. The formation of 4-nitrophenolate was measured at 405 nm using a microtiter plate reader. The IC50 values were calculated.

The results of the in vitro tests are shown in tables 1 and 2 below.

TABLE 1

Test results

| Ex. No. | Compound | Kinase assay IC$_{50}$ (mol/l) | Cytokines IC$_{50}$ (mol/l) | |
| --- | --- | --- | --- | --- |
| | | | TNF α | IL-1β |
| 21 | 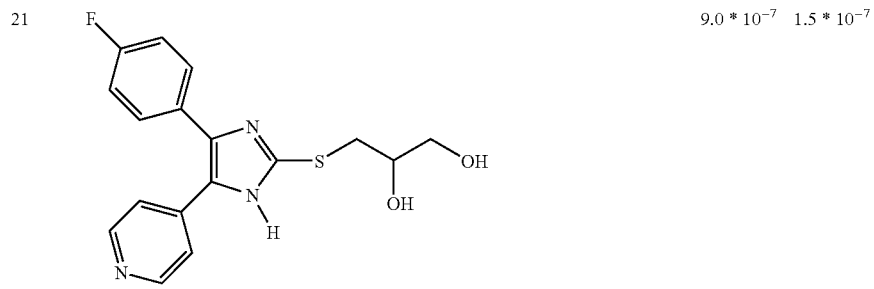 | | $9.0 * 10^{-7}$ | $1.5 * 10^{-7}$ |

TABLE 1-continued
Test results
| | | |
|---|---|---|
| 22 | 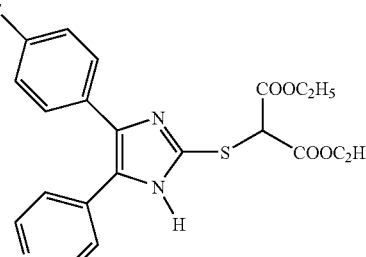 | $3.6 * 10^{-7}$  $5.4 * 10^{-7}$ |
| 23 | 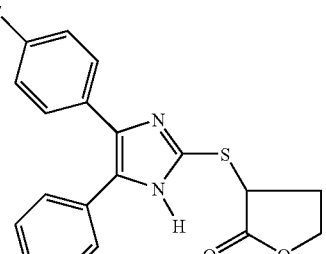 | $3.8 * 10^{-6}$  $1.9 * 10^{-7}$ |
| 24 | 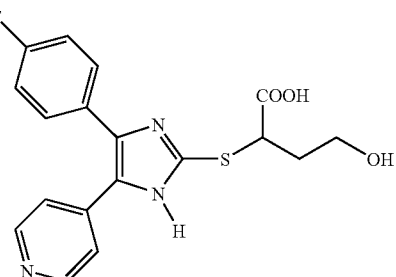 | $3.8 * 10^{-6}$  $1.4 * 10^{-7}$ |
| 25 | 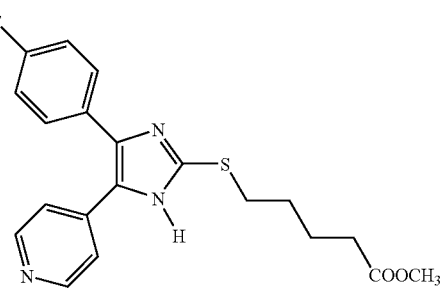 | 28% at $10^{-5}$ mol/l   $1.45 * 10^{-6}$ |
| 25a | 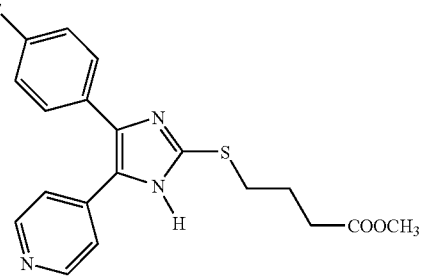 | 38% at $10^{-5}$ mol/l   $7.5 * 10^{-7}$ |

TABLE 1-continued

Test results

| | | | | |
|---|---|---|---|---|
| 25b | [4-(4-fluorophenyl)-5-(pyridin-4-yl)-1H-imidazol-2-ylthio, CH2-CH=CH-COOCH3] | $1.1 * 10^{-6}$ | $6.5 * 10^{-7}$ | |
| 25c | [4-(4-fluorophenyl)-5-(pyridin-4-yl)-1H-imidazol-2-ylthio, CH2-COOCH3] | $7.5 * 10^{-7}$ | $2.1 * 10^{-6}$ | $3.2 * 10^{-7}$ |
| 25d | [4-(4-fluorophenyl)-5-(pyridin-4-yl)-1H-imidazol-2-ylthio, (CH2)3-phthalimide] | $5.5 * 10^{-6}$ | — | $9.2 * 10^{-7}$ |
| 25e | [4-(4-fluorophenyl)-5-(pyridin-4-yl)-1H-imidazol-2-ylthio, CH2-C(=O)-OC2H5] | $9.75 * 10^{-7}$ | $9.5 * 10^{-6}$ | $7.0 * 10^{-7}$ |
| 26 | [4-(4-fluorophenyl)-5-(pyridin-4-yl)-1-methyl-1H-imidazol-2-ylthio, CH2-C(=O)-CH3] | 37.0% at $10^{-5}$ mol/l | $8.3 * 10^{-8}$ | |

TABLE 1-continued

| | Test results | | | |
|---|---|---|---|---|
| 27 | [4-(4-fluorophenyl)-5-(pyridin-4-yl)-1-methyl-1H-imidazol-2-ylthio]-N,N-dimethylacetamide | 29.0% at $10^{-5}$ mol/l | $3 * 10^{-6}$ | $1.5 * 10^{-7}$ |
| 28 | 3-[4-(4-fluorophenyl)-5-(pyridin-4-yl)-1-methyl-1H-imidazol-2-ylthio]pentane-2,4-dione | $9.5 * 10^{-6}$ | | |
| 29 | ethyl 2-[4-(4-fluorophenyl)-5-(pyridin-4-yl)-1-methyl-1H-imidazol-2-ylthio]-3-oxobutanoate | 13.8% at $10^{-5}$ mol/l | | |
| 30 | ethyl 5-[4-(4-fluorophenyl)-5-(pyridin-4-yl)-1-methyl-1H-imidazol-2-ylthio]-3-oxopentanoate | $4.8 * 10^{-6}$ mol/l | | |

| Ex. No. | Compound | Kinase assay $IC_{50}$ (mol/l) |
|---|---|---|
| 31 | methyl (E)-4-[4-(4-fluorophenyl)-5-(pyridin-4-yl)-1-methyl-1H-imidazol-2-ylthio]but-2-enoate | $4.2 * 10^{-5}$ |

TABLE 1-continued
Test results
| | | |
|---|---|---|
| 32 | 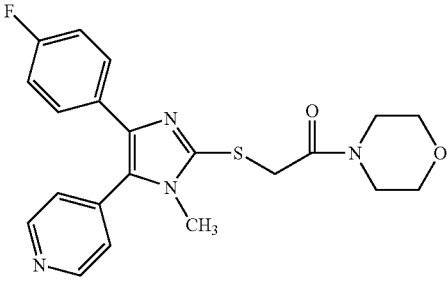 | $9.0 * 10^{-5}$ |
| 33 | 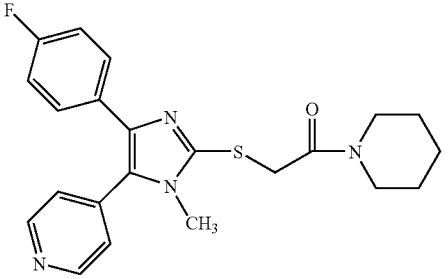 | $7.5 * 10^{-5}$ |
| 36 | 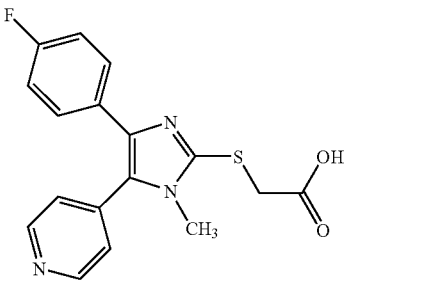 | $1.6 * 10^{-6}$ mol/l |
| 37 | 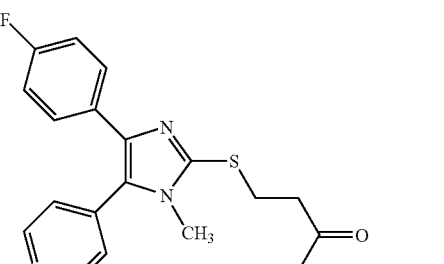 | $2 * 10^{-6}$ mol/l |
| 38 | 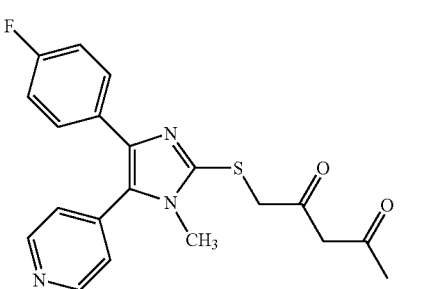 | 12.22% at $10^{-6}$ mol/l |

TABLE 1-continued
Test results
| | | |
|---|---|---|
| 39 | 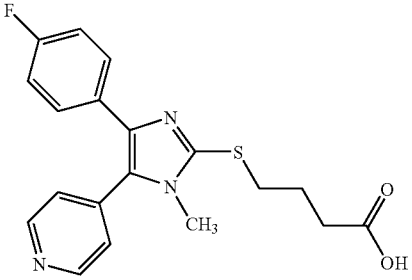 | $5 * 10^{-6}$ mol/l |
| 40 | 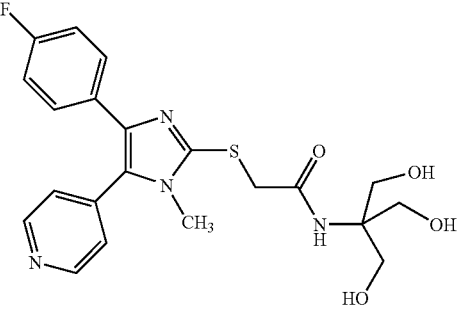 | $8 * 10^{-7}$ mol/l |
| 41 | 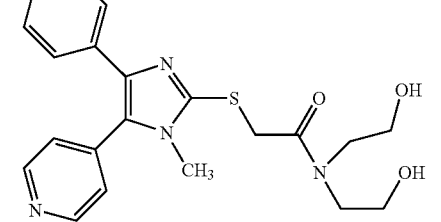 | $4.1 * 10^{-7}$ mol/l |
| 42 | 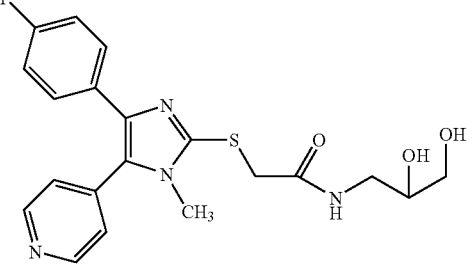 | 90.4% at $10^{-4}$ mol/l |
| 43 | 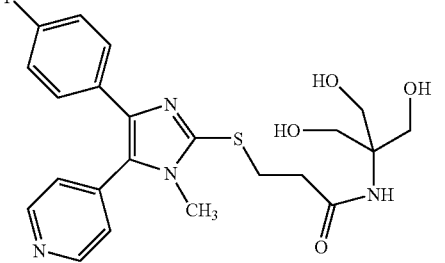 | $1.2 * 10^{-5}$ mol/l |

TABLE 1-continued

Test results

| | | |
|---|---|---|
| 44 | [4-(4-fluorophenyl)-5-(pyridin-4-yl)-1-methyl-imidazol-2-yl]thio-propanoyl-N,N-bis(2-hydroxyethyl)amide structure | $3 * 10^{-5}$ mol/l |
| 45 | [4-(4-fluorophenyl)-5-(pyridin-4-yl)-1-methyl-imidazol-2-yl]thio-2-oxo-ethyl ethyl ester structure | $7 * 10^{-6}$ mol/l |
| 46 | [4-(4-fluorophenyl)-5-(pyridin-4-yl)-1-methyl-imidazol-2-yl]thio-2-chloroethyl structure | $3.6 * 10^{-7}$ mol/l |
| 47 | [4-(4-fluorophenyl)-5-(pyridin-4-yl)-1-methyl-imidazol-2-yl]thio-3-chloropropyl structure | $3.4 * 10^{-6}$ mol/l |
| 48 | [4-(4-fluorophenyl)-5-(pyridin-4-yl)-1-methyl-imidazol-2-yl]thio-ethyl phthalimide structure | 30.9% at $10^{-6}$ mol/l |

TABLE 1-continued
Test results
| 49 | 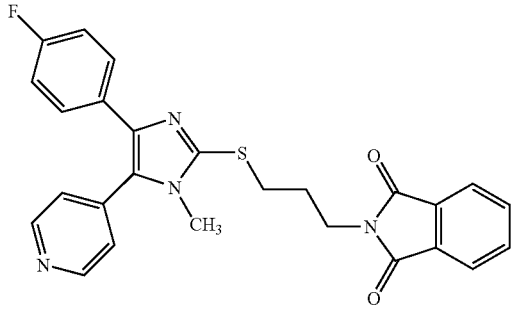 | $2.4 * 10^{-6}$ mol/l |
| 52 | 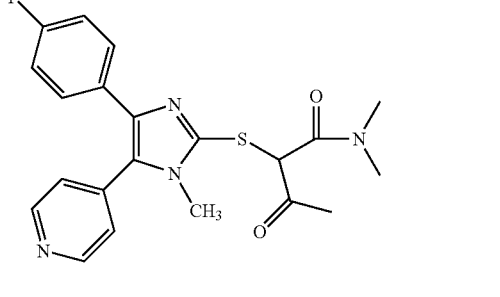 | 25.2% at $10^{-5}$ mol/l |
| 59 | 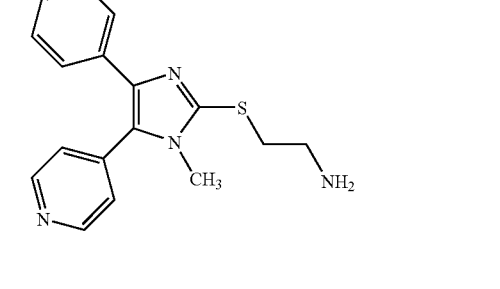 | $1.8 * 10^{-6}$ mol/l |
| 60 | 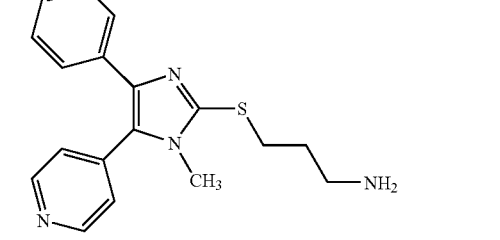 | $1.4 * 10^{-6}$ mol/l |

TABLE 2

| Ex. No. | Compound | p38α % inhibition at 1 μM p38α IC$_{50}$: |
|---|---|---|
| 57 | 4-(4-fluorophenyl)-2-[(2,3-dihydroxypropyl)thio]-1-methyl-5-(pyridin-4-yl)-1H-imidazole | IC$_{50}$ = 3.6 |
| 67 | N-{4-[4-(4-fluorophenyl)-2-[(2,3-dihydroxypropyl)thio]-1-methyl-1H-imidazol-5-yl]pyridin-2-yl}acetamide | 77% IC$_{50}$ = 0.43 |
| 69 | N-{4-[4-(4-fluorophenyl)-2-({2-[bis(2-hydroxyethyl)amino]-2-oxoethyl}thio)-1-methyl-1H-imidazol-5-yl]pyridin-2-yl}acetamide | 90% IC$_{50}$ = 0.25 |
| 70 | ethyl 3-{[4-(4-fluorophenyl)-5-(2-acetamidopyridin-4-yl)-1-methyl-1H-imidazol-2-yl]thio}propanoate | 83% IC$_{50}$ = 0.53 |

TABLE 2-continued

| Ex. No. | Compound | p38α % inhibition at 1 μM p38α IC$_{50}$: |
|---|---|---|
| 71 | [structure: 4-(4-fluorophenyl)-5-(2-aminopyridin-4-yl)-1-methyl-2-[(N,N-bis(2-hydroxyethyl)aminocarbonylmethyl)thio]imidazole] | 76% IC$_{50}$ = 0.90 |
| 72 | [structure: 4-(4-fluorophenyl)-5-(2-aminopyridin-4-yl)-1-methyl-2-(2-carboxyethylthio)imidazole] | 64% |

The compounds according to the invention and the processes for their preparation are now described in more detail using the examples below, without limiting the invention.

EXAMPLES

Example 1

4-(4-fluorophenyl)-1-methyl-5-(4-pyridyl)-2-thioimidazole a) 2-Cyano-2-(4-fluorophenyl)-1-(4-pyridyl)ethane 250 ml of dry ethanol were added dropwise to metallic sodium (17.3 g/0.7 mol). Ethyl isonicotinate (75.8 g/0.5 mol) and 4-fluorophenylacetonitrile (67.6 g/0.5 mol) were then added dropwise, and the mixture was subsequently heated under reflux for 15 min. After cooling, 600 ml of distilled water were added to the mixture. When the mixture was acidified to pH 1 using concentrated hydrochloric acid (HCl), the desired compound 2-cyano-2-(4-fluorophenyl)-1-(4-pyridyl)ethane precipitated as a yellow precipitate. The precipitate was filtered off, washed with distilled water and dried under reduced pressure over phosphorus pentoxide (P2O5). The yield was 85.0 g (62%).

b) 2-(4-Fluorophenyl)-1-(4-pyridyl)ethanone

2-Cyano-2-(4-fluorophenyl)-1-(4-pyridyl)ethane (40.6 g/0.15 mol) from example 1a was suspended in 300 ml of 48% strength hydrobromic acid (HBr), and the reaction mixture was heated under reflux for 18 h. After cooling, the mixture was adjusted to pH 9 using aqueous ammonia. The compound mentioned in the title, which precipitated during this operation, was filtered off, washed with distilled water and dried under reduced pressure over P2O5. The yield was 25.6 g (80%).

c) 2-(4-Fluorophenyl)-1-(4-pyridyl)-α-hydroxyiminoethanone 15.0 g (0.07 mol) of 2-(4-fluorophenyl)-1-(4-pyridyl)ethanone from example 1b were dissolved in 70 ml of glacial acetic acid. A solution of 4.8 g (0.07 mol) of NaNO2 in 11 ml of water was slowly added dropwise to the initial charge, and the reaction mixture was stirred at room temperature. After 3 h, 400 ml of distilled water were added, and the mixture was stirred at room temperature for another 3 h. The compound (3) mentioned in the title precipitated out. The compound was filtered off, washed with distilled water and dried under reduced pressure over P2O5. The yield was 15.2 g (90%).

d) 4-(4-Fluorophenyl)-1-methyl-5-(4-pyridyl)imidazole N-oxide 2.0 g of 2-(4-fluorophenyl)-1-(4-pyridyl)-α-hydroxyiminoethanone from example 1c above and twice the equivalent amount of 1,3,5-trimethylhexahydro-1,3,5-triazine were dissolved in 20 ml of dry ethanol and heated under reflux for 10 h. After cooling, the ethanol was removed using a rotary evaporator. The slightly oily residue solidified on addition of diethyl ether. The precipitate was filtered off and dried under reduced pressure. The yield was 82%.

e) 4-(4-Fluorophenyl)-1-methyl-5-(4-pyridyl)imidazole-2-thione 0.5 g of 5-(4-fluorophenyl)-4-(4-pyridyl)-3-methylimidazole N-oxide from example 1d were dissolved in 20 ml of CHCl3, and the reaction mixture was cooled in an ice-bath. An equimolar solution of 2,2,4,4-tetramethyl-3-thionocyclobutanone in CHCl3 was slowly added dropwise to the initial charge, and the mixture was then stirred in the ice-bath for 30 min. The ice-bath was removed, and stirring was continued at room temperature for 1 h. The solvent was then removed using a rotary evaporator, and the solid residue was triturated in diethyl ether. The precipitate was filtered off and dried under reduced pressure. The yield was 98%.

IR: 1/λ (cm−1)=1601, 1506, 1229, 1004, 843, 832

1H NMR (d6-DMSO, ppm): 12.95 (bs, 1H), 8.69-8.66 (m, 2H), 7.45-7.42 (m, 2H), 7.27-7.12 (m, 4H), 3.39 (s, 3H)

Example 2

1-Ethyl-4-(4-fluorophenyl)-5-(4-pyridyl)-2-thioimidazole a) 1-Ethyl-4-(4-fluorophenyl)-5-(4-pyridyl)imidazol-2-one

Initially, 2-(4-fluorophenyl)-1-(4-pyridyl)-α-hydroxyiminoethanone was prepared as described in example 1, steps (a) to (c). 4.0 g of the iminoethanone were then, together with the equimolar amount of ethylamine and the equimolar amount of formaldehyde (36% strength aqueous solution), heated under reflux for 4 h. After cooling, the reaction mixture was neutralized using aqueous ammonia and extracted three times with CH2Cl2. The organic phases were combined and dried over Na2SO4. The drying agent was filtered off and the solvent was removed using a rotary evaporator. The slightly oily residue was solidified by addition of diethyl ether. The precipitate was filtered off and dried under reduced pressure. The yield was 63%.

b) 2-Chloro-1-ethyl-4-(4-fluorophenyl)-5-(4-pyridyl)imidazole 35 ml of POCl3 and a small amount of NH4Cl were added to 2.0 g of 1-ethyl-4-(4-fluorophenyl)-5-(4-pyridyl)imidazol-2-one, and the reaction mixture was heated under reflux for 9 h. After cooling, most of the excess POCl3 was distilled off, and distilled water was carefully added to the residue. The mixture was neutralized using 20% strength NaOH, resulting in the precipitation of the title compound. The precipitate was filtered off and dried over P2O5 under reduced pressure. Yield: 81%.

c) 1-Ethyl-4-(4-fluorophenyl)-5-(4-pyridyl)imidazole-2-thione

NaH (4.5 eq.) was suspended in 10 ml of DMF, and 4-chlorobenzylthiol (4.5 eq.) was slowly added dropwise. The reaction mixture was stirred at room temperature for 45 min. 2.0 g of the 2-chloro-1-ethyl-4-(4-fluorophenyl)-5-(4-pyridyl)imidazole obtained in the step above were then added. The mixture was heated under reflux for 10 h. After cooling, distilled water was added to the mixture, the pH was adjusted to 1 using concentrated HCl and the mixture was washed six times with diethyl ether. Neutralization of the aqueous phase with 20% strength NaOH resulted in the precipitation of the title compound. The precipitate was filtered off and dried over P2O5 under reduced pressure. Purification was by recrystallization. The yield was 50%.

IR: 1/λ (cm−1)=3059, 1587, 1498, 1220, 837, 814

1H NMR (CDCl3, ppm): 12.63 (bs, 1H), 8.74-8.72 (m, 2H), 7.27-7.17 (m, 4H), 7.0-6.90 (m, 2H), 4.08 (q, 2H, J=7.1 Hz), 1.21 (t, 3H, J=7.1 Hz)

Example 3A

4-(4-Fluorophenyl)-1-n-propyl-5-(4-pyridyl)-2-thioimidazole

The process of example 1 was employed, where step d) the 2-(4-fluorophenyl)-1-(4-pyridyl)-α-hydroxyiminoethanone was reacted with twice the equivalent amount of 1,3,5-tri-n-propylhexahydro-1,3,5-triazine.

The yield was in the range of 60-91%.

IR: 1/λ (cm−1)=2932, 1586, 1500, 1221, 831, 814

1H NMR (CDCl3, ppm): 12.47 (bs, 1H), 8.76-8.73 (m, 2H), 7.26-7.13 (m, 4H), 7.0-6.96 (m, 2H), 3.98 (t, 2H, J=7.8 Hz), 1.65 (m, 2H), 0.82 (t, 3H, J=7.4 Hz)

Example 3B

4-(4-Fluorophenyl)-1-n-propyl-5-(4-pyridyl)-2-thioimidazole

Alternatively, to prepare the title compound, the process of example 2 was employed, where step a) 2-(4-fluorophenyl)-1-(4-pyridyl)-α-hydroxyiminoethanone was reacted with the equimolar amount of n-propylamine.

The yield was in the range of 32-72%.

Example 4

4-(4-Fluorophenyl)-1-isopropyl-5-(4-pyridyl)-2-thioimidazole

To prepare the title compound, the process of example 2 was employed, where in step a) 2-(4-fluorophenyl)-1-(4-pyridyl)-α-hydroxyiminoethanone was reacted with the equimolar amount of isopropylamine.

IR: 1/λ (cm−1)=3040, 1584, 1500, 1230, 841, 819

1H NMR (CDCl3, ppm): 11.73 (bs, 1H), 8.76-8.74 (m, 2H,), 7.28 (m, 2H), 7.17-7.10 (m, 2H), 7.0-6.92 (m, 2H), 4.89 (m, 1H), 1.48 (s, 3H), 1.45 (s, 3H)

Example 5

1-Cyclohexyl-4-(4-fluorophenyl)-5-(4-pyridyl)-2-thioimidazole

To prepare the title compound, the process of example 2 was used, where in step a) 2-(4-fluorophenyl)-1-(4-pyridyl)-α-hydroxyiminoethanone was reacted with the equimolar amount of cyclohexylamine.

IR: 1/λ (cm−1)=2934, 1560, 1505, 1228, 842

1H NMR (CDCl3, ppm): 11.32 (bs, 1H), 8.76-8.73 (m, 2H), 7.30-7.31 (m, 2H), 7.15-7.08 (m, 2H), 7.01-6.92 (m, 2H), 4.60-4.25 (m, 1H), 2.0-1.18 (m, 10H)

Example 6

1-Cyclopropyl-4-(4-fluorophenyl)-5-(4-pyridyl)-2-thioimidazole

The same process as in example 1 was used, where in step d) the 2-(4-fluorophenyl)-1-(4-pyridyl)-α-hydroxyiminoethanone was reacted with twice the equivalent amount of 1,3,5-tricyclopropylhexahydro-1,3,5-triazine.

IR: 1/λ (cm−1)=3013, 1589, 1515, 1499, 1487, 1223, 830, 685

1H NMR (CDCl3, ppm): 12.76 (bs, 1H), 8.68-8.65 (m, 2H), 7.26-7.19 (m, 4H), 7.07-6.99 (m, 2H), 3.12-3.08 (m, 1H), 1.02-0.95 (m, 2H), 0.76-0.71 (m, 2H)

Example 7

4-(4-Fluorophenyl)-1-phenyl-5-(4-pyridyl)-2-thioimidazole

To prepare the title compound, the process of example 2 was employed, where in step a) 2-(4-fluorophenyl)-1-(4-pyridyl)-α-hydroxyiminoethanone was reacted with the equimolar amount of aniline.

IR: 1/λ (cm−1)=2880, 1597, 1504, 1227, 844, 825

1H NMR (CDCl3, ppm): 11.58 (bs, 1H), 8.48-8.41 (m, 2H), 7.78-6.74 (m, 11H)

Example 8

1-Benzyl-4-(4-fluorophenyl)-5-(4-pyridyl)-2-thioimidazole

To prepare the title compound, the process of example 2 was employed, where in step a) 2-(4-fluorophenyl)-1-(4-pyridyl)-α-hydroxyiminoethanone was reacted with the equimolar amount of benzylamine.

IR: 1/λ (cm−1)=3032, 1587, 1497, 1225, 1158, 837, 816

1H NMR (CDCl3, ppm): 12.88 (bs, 1H), 8.56-8.53 (m, 2H), 7.27-6.90 (m, 11H), 5.28 (s, 2H)

Example 9

1-Dimethylaminophenyl-4-(4-fluorophenyl)-5-(4-pyridyl)-2-thioimidazole

To prepare the title compound, the process of example 2 was employed, where in step a) 2-(4-fluorophenyl)-1-(4-pyridyl)-α-hydroxyiminoethanone was reacted with the equimolar amount of 4-dimethylaminobenzylamine.

IR: 1/λ (cm−1)=2891, 1606, 1500, 1357, 1225, 835, 816

1H NMR (d6-DMSO, ppm): 13.05 (bs, 1H), 8.43-8.41 (m, 2H), 7.37-7.03 (m, 8H), 6.98-6.60 (m, 2H), 2.89 (s, 6H)

Example 10

4-(4-Fluorophenyl)-1-(3-pyridyl)-5-(4-pyridyl)-2-thioimidazole

To prepare the title compound, the process of example 2 was employed, where in step a) 2-(4-fluorophenyl)-1-(4-pyridyl)-α-hydroxyiminoethanone was reacted with the equimolar amount of 3-pyridylamin.

IR: 1/λ (cm−1)=3035, 1597, 1478, 1433, 1433, 1224, 813, 708

1H NMR (d6-DMSO, ppm): 13.34 (s, 1H), 8.54-8.45 (m, 4H), 7.76-7.75 (m, 1H), 7.40-7.13 (m, 7H)

Example 11

1-Dimethylaminoethyl-4-(4-fluorophenyl)-5-(4-pyridyl)-2-thioimidazole

The same process as in example 1 was used, where in step d) the 2-(4-fluoro-phenyl)-1-(4-pyridyl)-α-hydroxyiminoethanone was reacted with twice the equivalent amount of 1,3,5-tri(2-di methylaminoethyl)hexahydro-1,3,5-triazine.

IR: 1/λ (cm−1)=2772, 1597, 1503, 1225, 835, 815

1H NMR (CDCl3, ppm): 8.74-8.72 (m, 2H), 7.30-7.17 (m, 4H), 7.04-6.94 (m, 2H), 4.13 (t, 2H, J=6.8 Hz), 2.56 (t, 2H, J=6.7 Hz), 2.11 (s, 6H)

Example 12

4-(4-Fluorophenyl)-5-(4-pyridyl)-1-(2,2,6,6-tetramethylpiperidin-4-yl)-2-thioimidazole The same process as in example 1 as employed, where in step d) the 2-(4-fluorophenyl)-1-(4-pyridyl)-α-hydroxyiminoethanone was reacted with twice the molar amount of 2,2,6,6-tetramethyl-4-methyleneaminopiperidine.

IR: 1/λ (cm−1)=2964, 1587, 1498, 1352, 1234, 838, 815

Example 13

1-Dimethylaminopropyl-4-(4-fluorophenyl)-5-(4-pyridyl)-2-thioimidazole

The same process as in example 1 was employed, where in step d) the 2-(4-fluorophenyl)-1-(4-pyridyl)-α-hydroxyiminoethanone was with twice the equivalent amount of 1,3,5-tri(3-dimethylaminopropyl)hexahydro-1,3,5-triazine.

Example 14

4-(4-Fluorophenyl)-1-(3-N-morpholinopropyl)-5-(4-pyridyl)-2-thioimidazole

The same process as in example 1 was employed, where in step d) the 2-(4-fluorophenyl)-1-(4-pyridyl)-α-hydroxyiminoethanone was reacted with twice the equivalent amount of 1,3,5-tri(N-morpholinopropyl)hexahydro-1,3,5-triazine.

IR: 1/λ (cm−1)=2847, 1502, 1233, 1114, 842, 817

1H NMR (CDCl3, ppm): 12.11 (bs, 1H), 8.75-8.71 (m, 2H), 7.26-7.18 (m, 4H), 7.05-6.95 (m, 2H), 4.15-4.07 (m, 2H), 3.61-3.57 (m, 4H), 2.32-2.23 (m, 6H), 1.86-1.75 (m, 2H)

Example 15

4-(4-Fluorophenyl)-1-(4-methylsulfanylphenyl)-5-(4-pyridyl)-2-thioimidazole The same process as in example 1 was employed, where in step d) the 2-(4-fluorophenyl)-1-(4-pyridyl)-α-hydroxyiminoethanone was reacted with twice the equivalent amount of 1,3,5-tri(4-methylsulfanylphenyl)hexahydro-1,3,5-triazine.

IR: 1/λ (cm−1)=2693, 1597, 1495, 1220, 844, 817

1H NMR (CDCl3, ppm): 12.43 (bs, 1H), 8.47-8.44 (m, 2H), 7.32-7.12 (m, 6H), 7.06-6.97 (m, 2H), 6.90-6.87 (m, 2H), 2.50 (s, 3H)

Example 16

4-(4-Fluorophenyl)-1-N-morpholinoethyl-5-(4-pyridyl)-2-thioimidazole

The same process as in example 1 was employed, where in step d) the 2-(4-fluorophenyl)-1-(4-pyridyl)-α-hydroxyiminoethanone was reacted with twice the equivalent amount of 1,3,5-tri(N-morpholinoethylhexahydro-1,3,5-triazine.

IR: $1/\lambda$ (cm−1)=2813, 1599, 1508, 1232, 1117, 850, 835
1H NMR (d6-DMSO): 12.91 (bs, 1H), 8.71-8.68 (m, 2H), 7.49-7.46 (m, 2H), 7.25-7.16 (m, 4H), 4.04 (t, 2H, J=Hz), 2.40 (t, 2H, J=Hz), 2.16 (t, 4H, J=3.8 Hz)

Example 17

4-(4-Fluorophenyl)-1-(3-hydroxypropyl)-5-(4-pyridyl)-2-thioimidazole

The same process as in example 1 was employed, where in step d) the 2-(4-fluorophenyl)-1-(4-pyridyl)-α-hydroxyiminoethanone was reacted with twice the equivalent amount of 1,3,5-tri(3-hydroxypropyl)hexahydro-1,3,5-triazine.

IR: $1/\lambda$ $(cm^{-1})$=3049, 2926, 1499, 1223, 1162, 1061, 838
$^1$H NMR ($d_6$-DMSO, ppm): 12.98 (s, 1H), 8.71-8.68 (m, 2H), 7.47-7.44 (m, 2H), 7.29-7.12 (m, 4H), 4.47-4.43 (bs, 1H), 3.97 (t, 2H, J=7.4 Hz), 3.27 (t, 2H, J=6.2 Hz), 1.68-1.54 (m, 2H)

Example 18

1-(1-Benzylpiperidin-4-yl)-4-(4-fluorophenyl)-5-(4-pyridyl)-2-thioimidazole

The same process as in example 1 was employed, where in step d) the 2-(4-fluorophenyl)-1-(4-pyridyl)-α-hydroxyiminoethanone was reacted with twice the molar amount of 1-benzyl-4-methyleneaminopiperidine.

IR: $1/(cm^{-1})$=2903, 1504, 1247, 1227, 853, 741
$^1$H NMR ($d_6$-DMSO): 12.93 (s, 1H), 8.73-8.70 (m, 2H), 7.50-7.47 (m, 2H), 7.29-7.11 (m, 9H), 3.96-4.12 (m, 1H), 3.38 (s, 2H), 3.85-3.75 (m, 2H), 2.31-2.18 (m, 2H), 1.93-1.64 (m, 4H)

Example 19

1-Allyl-4-(4-fluorophenyl)-5-(4-pyridyl)-2-thioimidazole

The same process as in example 1 was employed, where in step d) the 2-(4-fluorophenyl)-1-(4-pyridyl)-α-hydroxyiminoethanone was reacted with twice the equivalent amount of 1,3,5-tri(prop-2-en-1-yl)hexahydro-1,3,5-triazine.

IR: $1/\lambda$ $(cm^{-1})$=2695, 1700, 1600, 1506, 1421, 1227, 1005, 934, 927, 841, 829, 817
$^1$H NMR (CDCl$_3$, ppm): 12.49 (bs, 1H), 8.72-8.65 (m, 2H), 7.29-7.22 (m, 4H), 7.04-6.96 (m, 2H), 6.00-5.81 (m, 1H), 5.25-5.19 (m, 1H), 5.02-4.93 (m, 1H), 4.66-4.64 (m, 2H)

Example 20

5-(4-Fluorophenyl)-4-pyridin-4-yl-1H-imidazole-2-thiol a) 2-(4-Fluorophenyl)-3-hydroxy-3-pyridin-4-ylacrylonitrile

30% strength sodium methoxide solution (0.7 mol/57.7 g) was added to 100 ml of absolute methanol. 4-Fluorophenylacetonitrile (0.5 mol/67.7 g) and ethyl isonicotinate (0.5 mol/75.8 g) were added successively. The reaction mixture was heated under reflux with stirring for 20 min. 600 g of ice were then added to the mixture, and stirring was continued for 10 min. After acidification with concentrated HCl, the title compound was obtained as a yellow precipitate. The precipitate was filtered off, washed with H$_2$O and dried over P$_2$O$_5$ under reduced pressure. Yield: 96.5 g (70%)

$^1$H-NMR ([D$^6$]DMSO): (CDCl$_3$)(1:1) δ[ppm]=8.8 (d, 2H, AA' 4-Pyr), 7.8 (m, 2H, 4-F-Phe), 7.7 (d, 2H, BB' 4-Pyr), 7.1 (m, 2H, 4-F-Phe), enol signal not visible.

IR: 2198 cm−1, 1706 cm−1, 1604 cm−1, 1503 cm−1, 1411 cm−1, 1336 cm−1, 1300 cm−1, 1233 cm$^{-1}$, 1161 cm$^{-1}$, 1065 cm$^{-1}$, 1019 cm$^{-1}$, 856 cm$^{-1}$, 805 cm$^{-1}$, 760 cm$^{-1}$, 695 cm$^{-1}$, b) 2-(4-Fluorophenyl)-1-pyridin-4-ylethanone 2-(4-Fluorophenyl)-3-hydroxy-3-pyridin-4-ylacrylonitrile (0.15 mol/40.6 g) was dissolved in 290 ml of 48% HBr. With vigorous stirring, the reaction mixture was heated under reflux for 24 h. 500 g of ice were then added to the reaction mixture, and the mixture was stirred for another 2 h. After addition of a further 300 g of ice and neutralization of the mixture to pH 7 using concentrated NH$_3$ and a further 60 min of stirring, the title compound was obtained as an ochre-brown precipitate. The precipitate was filtered off, washed with H$_2$O and dried over P$_2$O$_5$ under reduced pressure. Yield: 16.1 g (50%)

$^1$H-NMR (CDCl$_3$): δ [ppm]=8.8 (d, 2H, AA' 4-Pyr), 7.8 (d, 2H, BB' 4-Pyr, 7.2 (m, 2H, 4-F Phe), 7.0 (m, 2H, 4-F-Phe), 4.3 (s, 2H, —CH2-)

c) 1-(4-Fluorophenyl)-2-pyridin-4-ylethane-1,2-dione-1-oxime 2-(4-Fluorophenyl)-1-(4-pyridinyl)ethanone (0.1 mol/25.2 g) was suspended in 330 ml of methanol. After addition of sodium acetate (0.44 mol/36.1 g) and hydroxylamine*HCl (0.32 mol/22.0 g), the reaction mixture was heated under reflux with stirring for 1 h. On cooling in an ice bath, the title compound was obtained as a white precipitate. The precipitate was filtered off, washed with H$_2$O and dried over P$_2$O$_5$ under reduced pressure. Yield: 14.3 g (62%)

$^1$H-NMR (CDCl$_3$): δ [ppm]=11.7 (s, 1H, —OH), 8.6 (d, 2H, AA', 4-Pyr), 7.5 (d, 2H, BB' 4-Pyr), 7.2 (m, 2H, 4-F-Phe), 6.9 (m, 2H, 4-F-Phe), 4.2 (s, 2H, —CH$_2$—)

IR: 2727 cm$^{-1}$, 1597 cm$^{-1}$, 1504 cm$^{-1}$, 1442 cm$^{-1}$, 1413 cm$^{-1}$, 1334 cm$^{-1}$, 1306 cm$^{-1}$, 1223 cm$^{-1}$, 1159 cm$^{-1}$, 1094 cm$^{-1}$, 1075 cm$^{-1}$, 1006 cm$^{-1}$, 971 cm$^{-1}$, 933 cm$^{-1}$, 837 cm$^{-1}$, 827 cm$^{-1}$, 814 cm$^{-1}$, 782 cm$^{-1}$, 766 cm$^{-1}$, 731 cm$^{-1}$, 694 cm$^{-1}$, 668 cm$^{-1}$ d) 2-4(Fluorophenyl)-1-(4-pyridinyl)ethanone-O-[(4-methylphenyl)sulfonyl]oxime Under an atmosphere of argon, 2-(4-fluorophenyl)-1-(4-pyridinyl)ethaneoxime (0.04 mol/10.1 g) was dissolved in 50 ml of absolute pyridine. In an ice bath, the solution was cooled to 0° C., and toluenesulfonyl chloride (0.05 mol/10.1 g) was added a little at a time with stirring. After the addition had ended, the reaction mixture was stirred at room temperature for 24 h. The mixture was then poured into 500 ml of ice-water. With stirring, the title compound was obtained as a white precipitate. The precipitate was filtered off, washed with H$_2$O and dried in a drying cabinet at 50° C. Yield: 14.9 g (88%)

$^1$H-NMR (CDCl$_3$): δ [ppm]=8.6 (d, 2H, AA' 4-Pyr), 7.9 (m, 2H 4-Tos), 7.5 (d, 2H, BB' 4-Pyr), 7.4 (m, 2H 4-Tos), 7.1 (m, 2H 4-F-Phe), 6.9 (m, 2H 4-F-Phe), 4.1 (s, 2H —CH$_2$—), 2.5 (s, 3H —CH$_3$)

IR: 2753 cm$^{-1}$, 1597 cm$^{-1}$, 1505 cm$^{-1}$, 1414 cm$^{-1}$, 1335 cm$^{-1}$, 1224 cm$^{-1}$, 1094 cm$^{-1}$, 1075 cm$^{-1}$, 1007 cm$^{-1}$, 934 cm$^{-1}$, 838 cm$^{-1}$, 827 cm$^{-1}$, 815 cm$^{-1}$, 783 cm$^{-1}$, 767 cm$^{-1}$, 732 cm$^{-1}$, 668 cm$^{-1}$, 655 cm$^{-1}$, e) 5-(4-Fluorophenyl)-4-(4-pyridinyl)imidazole-2-thione Under an atmosphere of argon, 2-(4-fluorophenyl)-1-(4-pyridinyl)ethanone-O-[(4-methylphenyl)sulfonyl]oxime (0.03 mol/10.0 g) was dissolved in 60 ml of absolute ethanol. In an ice bath, the mixture was cooled to 0° C., and a freshly prepared solution of sodium (0.03 M/0.75 g) in 30 ml of absolute ethanol was added dropwise. The reaction mixture was stirred at 0° C. for 1.5 h. After addition of 500 ml of diethyl ether, stirring was continued for 30 min. The resulting precipitate was filtered off and washed 4× with in each case 50 ml of diethyl ether. The combined ether phase was extracted 3× with in each case 90 ml of HCl 10%. The aqueous extract was concentrated to 40 ml, and KSCN (0.05 mol/5.0 g) was added. With stirring, the reaction mixture was then heated under reflux for 1 h. When the mixture was neutralized using 270 ml of 5% strength NaHCO$_3$ solution, the title compound was obtained as a yellow precipitate. The precipitate was filtered off, washed with H$_2$O and dried in a drying cabinet at 60° C. Yield: 5.6 g (79%)

$^1$H-NMR ([D$^6$]DMSO): (CDCl$_3$) (1:1) δ [ppm]=12.7 (d, 2H NH), 8.5 (d, 2H, AA' 4-Pyr), 7.5 (m, 2H 4-F-Ph), 7.3 (d, 2H, BB' 4-Pyr), 7.1 (m, 2H 4-F-Phe)

IR: 1603 cm$^{-1}$, 1518 cm$^{-1}$, 1424 cm$^{-1}$, 1227 cm$^{-1}$, 1161 cm$^{-1}$, 1100 cm$^{-1}$, 1005 cm$^{-1}$, 845 cm$^{-1}$, 683 cm$^{-1}$,

General procedure for the synthesis of the 2-thioethers exemplified by 5-(4-fluorophenyl)-4-(4-pyridinyl)imidazole-2-thioethers:

Under an atmosphere of argon, 5-(4-fluorophenyl)-4-(4-pyridinyl)imidazole-2-thione (0.001 mol/0.271 g) was dissolved in 20 ml of absolute methanol. Sodium ethoxide (0.0012 mol/0.065 g) was then added and the mixture was stirred for 10 min. The bromoaliphatic compound (0.0011 mol) in question, dissolved in 10 ml of absolute methanol, was added dropwise to the initial charge. The mixture was then heated under reflux for 4 h and subsequently stirred at room temperature for 2 h. After neutralization with HCl 10% to pH 7, the liquid was removed under reduced pressure and the residue was worked up by column chromatography (mobile phase: CH$_2$Cl$_2$/EtOH 9:1; silica gel).

The following compounds were obtained by the above process:

Example 21

5-(4-Fluorophenyl)-4-(4-pyridinyl)imidazole-2-thio-1-propane-2,3-diol $^1$H-NMR ([D$^6$]DMSO) δ [ppm]=12.8 (s 1H NH), 8.5 (d, 2H AA' 4-Pyr), 7.5 (m, 2H, 4-F-Phe), 7.3 (d, 2H, BB'4-Pyr), 7.2 (m, 2H, 4-F-Phe), 5.3 (d, 1H, OH), 4.8 (t, 1H, OH), 3.7 (m, 2H CH$_2$—OH), 3.4 (m, 1H CH—OH), 3.1 (d, 2H CH$_2$)

IR: 3401 cm$^{-1}$, 1604 cm$^{-1}$, 1542 cm$^{-1}$, 1505 cm$^{-1}$, 1423 cm$^{-1}$, 1371 cm$^{-1}$, 1230 cm$^{-1}$, 1157 cm$^{-1}$, 1063 cm$^{-1}$, 1002 cm$^{-1}$, 968 cm$^{-1}$, 879 cm$^{-1}$, 832 cm$^{-1}$, 700 cm$^{-1}$, 679 cm$^{-1}$.

Example 22

Diethyl 5-(4-fluorophenyl)-4-(4-pyridinyl)imidazole-2-thio-2-malonate $^1$H-NMR ([D$^6$]DMSO) δ [ppm]=13.1 (s, 1H NH), 8.5 (d, 2H AA'4-Pyr), 7.5-7.1 (m, 6H, Ar), 5.3 (s, 1H CH), 4.2 (m, 2H O—CH$_2$), 1.9 (t, 3H —CH$_3$)

IR: 2962 cm$^{-1}$, 1758 cm$^{-1}$, 1604 cm$^{-1}$, 1506 cm$^{-1}$, 1366 cm$^{-1}$, 1233 cm$^{-1}$, 1171 cm$^{-1}$, 1096 cm$^{-1}$, 1023 cm$^{-1}$, 1002 cm$^{-1}$, 971 cm$^{-1}$, 835 cm$^{-1}$, 698 cm$^{-1}$, 680 cm$^{-1}$,

Example 23

5-(4-Fluorophenyl)-4-(4-pyridinyl)imidazole-2-thio-3-butyrolactone $^1$H-NMR ([D$^6$]DMSO) δ [ppm]=13.0 (s, 1H NH), 8.5 (d, 2H AA' 4-Pyr), 7.5-7.2 (m, 6H, AC), 7.3 (d, 2H BB' 4-Pyr), 7.2 (m, 2H 4-F-Phe), 4.5 (t, 1H S—CH), 4.3 (t, 2H O—CH$_2$), 2.7 (m, 2H —CH$_2$—)

IR: 2638 cm$^{-1}$, 1773 cm$^{-1}$, 1601 cm$^{-1}$, 1508 cm$^{-1}$, 1372 cm$^{-1}$, 1271 cm$^{-1}$, 1160 cm$^{-1}$, 1063 cm$^{-1}$, 1005 cm$^{-1}$, 968 cm$^{-1}$, 834 cm$^{-1}$, 814 cm$^{-1}$, 698 cm$^{-1}$, 685 cm$^{-1}$

Example 24

5-(4-Fluorophenyl)-4-(4-pyridinyl)imidazole-2-thio-2-butanoic acid-4-ol $^1$H-NMR ([D$^6$]DMSO) δ [ppm]=13.0 (s, 1H NH), 8.5 (d, 2H AA' 4-Pyr), 7.5 (m, 2H 4-F-Phe), 7.3 (d, 2H BB' 4-Pyr), 7.2 (m, 2H 4-F-Phe), 4.5 (t, 1H —CH), 4.3 (m, 2H —CH$_2$OH) 2.7 (m, 2H —CH$_2$—)

IR: 2607 cm$^{-1}$, 1771 cm$^{-1}$, 1601 cm$^{-1}$, 1507 cm$^{-1}$, 1412 cm$^{-1}$, 1372 cm$^{-1}$, 1217 cm$^{-1}$, 1160 cm$^{-1}$, 1063 cm$^{-1}$, 1005 cm$^{-1}$, 968 cm$^{-1}$, 833 cm$^{-1}$, 814 cm$^{-1}$, 697 cm$^{-1}$, 684 cm$^{-1}$

Example 25

Methyl 5-(4-fluorophenyl)-4-(4-pyridinyl)imidazole-2-thio-5-valerate $^1$H-NMR ([D$^6$]DMSO) δ [ppm]=12.7 (s, 1H NH), 8.4 (d, 2H AA' 4-Pyr), 7.5 (m, 2H 4-F-Phe), 7.3 (d, 2H BB' 4-Pyr), 7.2 (m, 2H 4-F-Phe), 3.5 (s, 3H —CH$_3$), 3.1 (t, 2H S—CH$_2$), 2.3 (t, 2H —CH$_2$—CO), 1.6 (m, 4H —CH$_2$—CH$_2$—)

IR: 2631 cm$^{-1}$, 1732 cm$^{-1}$, 1599 cm$^{-1}$, 1541 cm$^{-1}$, 1508 cm$^{-1}$, 1426 cm$^{-1}$, 1369 cm$^{-1}$, 1253 cm$^{-1}$, 1222 cm$^{-1}$, 1160 cm$^{-1}$, 1092 cm$^{-1}$, 1063 cm$^{-1}$, 1004 cm$^{-1}$, 966 cm$^{-1}$, 833 cm$^{-1}$, 815 cm$^{-1}$, 745 cm$^{-1}$, 727 cm$^{-1}$, 699 cm$^{-1}$, 686 cm$^{-1}$

Example 25a

Methyl 5-(4-fluorophenyl)-4-(4-pyridinyl)imidazole-2-thio-4-butyrate

IR (ATR) 2950, 2651, 1732, 1604, 1544, 1470, 1449, 1417, 1254, 1227, 1152, 1026, 1005, 829, 790, 708, 697, 681 cm$^{-1}$ $^1$H-NMR (DMSO-d$_6$) δ (ppm) 13.0 (s, 1H, NH), 8.5 (d, 2H, AA' 4-Pyr), 7.6-7.5 (m, 2H, 4-F-Phe), 7.3 (d, 2H, BB' 4-Pyr), 7.2-7.0 (m, 2H, 4-F-Phe), 3.5 (s, 3H, —CH$_3$), 3.1 (t, 2H, S—CH$_2$ 8 Hz), 2.4 (t, 2H, —CH$_2$—CO 6 Hz), 1.8 (t, 2H, —CH$_2$ 7 Hz))

Example 25b

Methyl 5-(4-fluorophenyl)-4-(4-pyridinyl)imidazole-2-thio-4-crotonate

IR (ATR) 3251, 1739, 1602, 1543, 1481, 1364, 1260, 1227, 1199, 1065, 1001, 972, 896, 852, 831, 759, 702, 673 cm$^{-1}$ $^1$H-NMR (DMSO-d$_6$) δ (ppm) 13.0 (s, 1H, NH), 8.4 (d, 2H, AA' 4-Pyr), 7.6-7.5 (m, 2H, 4-F-Phe), 7.4 (d, 2H, BB' 4-Pyr), 7.2-7.0 (m, 2H, 4-F-Phe), 4.9-4.8 (m, 1H, =CH—CO), 4.3-4.2 (m, 1H, =CH—), 3.7 (d, 2H, S—CH$_2$ 8 Hz), 3.5 (s, 3H, —CH$_3$ 7 Hz)

Example 25c

Methyl 5-(4-fluorophenyl)-4-(4-pyridinyl)imidazole-2-thio-2-acetate

IR (ATR) 2638, 1742, 1600, 1508, 1434, 1294, 1222, 1155, 1062, 1003, 967, 892, 836, 814, 699, 684 cm$^{-1}$ $^1$H-NMR (DMSO-d$_6$) δ (ppm) 12.9 (s, 1H, NH), 8.4 (d, 2H, AA' 4-Pyr), 7.7-7.6 (m, 2H, 4-F-Phe), 7.3 (d, 2H, BB' 4-Pyr), 7.2-7.1 (m, 2H, 4-F-Phe), 4.0 (s, 2H, S—CH$_2$ 8 Hz), 3.6 (s, 3H, —CH$_3$ 7 Hz)

Example 25d 5-(4-Fluorophenyl)-4-(4-pyridinyl)imidazole-2-thio-3-propyl-N-phthalimide IR (ATR) 2643, 1746, 1710, 1601, 1508, 1387, 1295, 1220, 1158, 1095, 1004, 968, 837, 815, 716, 696, 685 cm$^{-1}$, $^1$H-NMR (DMSO-d$_6$) δ (ppm) 12.8 (s, 1H, NH), 8.4 (d, 2H, AA' 4-Pyr), 7.8-7.7 (m, 4H, Phe), 7.6-7.5 (m, 2H, 4-F-Phe), 7.3 (d, 2H, BB' 4-Pyr), 7.2-7.1 (m, 2H, 4-F-Phe), 3.9 (t, 2H, S—CH$_2$ 6 Hz), 3.4 (t, 2H N—CH$_2$ 7 Hz)

Example 25e

Ethyl 5-(4-fluorophenyl)-4-(4-pyridinyl)imidazole-2-thio-2-acetate

IR (ATR) 2591, 1748, 1599, 1507, 1401, 1291, 1254, 1215, 1158, 1093, 1062, 1028, 1005, 965, 891, 836, 814, 747, 700, 686 cm$^{-1}$ $^1$H-NMR (DMSO-d$_6$) δ [ppm] 12.9 (s, 1H, NH), 8.4 (d, 2H, AA' 4-Pyr), 7.6-7.5 (m, 2H, 4-F-Phe), 7.4 (d, 2H, BB' 4-Pyr), 7.3-7.2 (m, 2H, 4-F-Phe), 4.2-4.1 (m, 2H, O—CH$_2$), 4.0 (s, 2H, S—CH$_2$), 1.2 (t, 3H, —CH$_3$ 7 Hz)

General procedure for preparing the imidazol-2-ylthioethers, exemplified by 5-(4-fluorophenyl)-4-(4-pyridinyl)-3-methylimidazol-2-ylthioethers a) 1-(4-Fluorophenyl)-2-pyridin-4-ylethane-1,2-dione-1-oxime 2-(4-Fluorophenyl)-1-pyridin-4-ylethanone (0.04 mol/8.6 g) (prepared as described in example 20, steps (a) and (b)) was dissolved in 80 ml of glacial acetic acid. NaNO$_2$ (0.04 mol/2.76 g), dissolved in the smallest amount of H$_2$O possible, was then added dropwise with ice-cooling and stirring. The mixture was then stirred at 0° C. for another 2 h. 500 ml of H$_2$O were then added, and the mixture was stirred at room temperature for another 1 h. The title compound precipitated as a white powder. The precipitate was filtered off, washed with H$_2$O and dried over P$_2$O$_5$ under reduced pressure. Yield: 5.9 g (60%)

$^1$H-NMR ([D$^6$]DMSO) δ [ppm]=13.0 (s, 1H —OH), 8.7 (d, 2H AA' 4-Pyr), 7.7 (m, 2H 4-F-Phe), 7.5 (d, 2H BB' 4-Pyr), 7.3 (m, 2H 4-F-Phe), 3.3 (s, 1H —CH)

b) 5-(4-Fluorophenyl)-1-methyl-4-pyridin-4-yl-1H-imidazol-2-ole 1-(4-Fluorophenyl)-2-pyridin-4-ylethane-1,2-dione-1-oxime (0.0123 mol/3.0 g) was suspended in 40 ml of absolute ethanol. N,N,N-Trimethyltriazine (0.0123 mol/1.59 g), dissolved in 10 ml of absolute ethanol, was added dropwise. With vigorous stirring, the mixture was then heated under reflux for 12 h. The mixture was then kept in a fridge for 12 h, which gave the title compound as a white precipitate. The precipitate was filtered off and washed with diethyl ether. Yield: 2.4 g (76.2%)

$^1$H-NMR ([D$^6$]DMSO): δ [ppm]=13.0 (s, 1H NH), 8.6 (d, 2H AA' 4-Pyr), 7.5 (m, 2H 4-F-Phe), 7.4 (d, 2H BB' 4-Pyr), 7.2 (m, 2H 4-F-Phe), 3.5 (s, 3H N—CH$_3$)

c) 5-(4-Fluorophenyl-1-methyl-4-pyridin-4-yl-1H-imidazole-2-thiol 4-(4-Fluorophenyl)-1-methyl-5-pyridin-4-yl-1H-imidazol-2-ole (0.01 mol/2.7 g) was dissolved in 40 ml of CHCl$_3$ and cooled in an icebath to 0° C. Tetramethylcyclobutane-1,3-thione (0.01 mol/1.77 g), dissolved in CHCl$_3$, was then added dropwise. The mixture was then stirred at 0° C. for 10 minutes and subsequently at room temperature for 1 h. The mixture was then concentrated under reduced pressure to give a brown viscous oil. After addition of diethyl ether, the title compound was obtained as a yellow precipitate. The precipitate was filtered off and washed with acetone and then with petroleum ether. Yield: 2.57 g (90%)

$^1$H-NMR ([D$^6$]DMSO): δ [ppm]=13.0 (s, 1H NH), 8.6 (d, 2H AA' 4-Pyr), 7.4 (m, 2H 4-F-Phe), 7.2 (d, 2H BB' 4-Pyr), 7.1 (m, 2H 4-F-Phe), 3.4 (s, 3H N—CH$_3$)

d) 5-(4-Fluorophenyl-1-methyl-4-pyridin-4-yl-1H-imidazole-2-thioether 5-(4-Fluorophenyl)-4-(4-pyridinyl)-3-methylimidazole-2-thione (0.002 mol/0.572 g) and K$_2$CO3 (0.0024 mol/0.188 g) were, with stirring, suspended in 40 ml of absolute tetrahydrofuran or methanol. The chloroaliphatic or bromoaliphatic compound in question (0.0021 M), dissolved in methanol or tetrahydrofuran, was then added dropwise. The mixture was stirred at room temperature for 24 h, the solvent was removed under reduced pressure and the residue was worked up by column chromatography (mobile phase: CH$_2$Cl$_2$/EtOH 9:1 or 9.5:0.5; silica gel). If appropriate, the product is taken up in ethyl acetate/CH$_2$CH$_2$, and five times the amount of petroleum ether is added. The precipitate formed is filtered off.

The following compounds were obtained by this process:

Example 26

1-[4-(4-Fluorophenyl)-1-methyl-5-pyridin-4-yl-1H-imidazol-2-ylsulfanyl]propan-2-one $^1$H-NMR (CDCl$_3$): δ [ppm]=8.7 (d, 2H AA' 4-Pyr), 7.3 (m, 2H 4-F-Phe), 7.2 (d, 2H BB' 4-Pyr), 6.9 (m, 2H 4-F-Phe), 4.1 (s, 2H S—CH$_2$), 3.5 (s, 3H N—CH$_3$), 2.4 (s, 3H CO—CH$_3$.

Example 27

1-[4-(4-Fluorophenyl)-1-methyl-5-pyridin-4-yl-1H-imidazol-2-ylsulfanyl]-N,N-dimethylacetamide $^1$H-NMR (CDCl$_3$): δ [ppm]=8.7 (d, 2H AA' 4-Pyr), 7.3 (m, 2H 4-F-Phe), 7.2 (d, 2H BB' 4-Pyr), 6.9 (m, 2H 4-F-Phe), 4.2 (s, 2H S—CH$_2$), 3.5 (s, 3H N—CH$_3$), 3.0 (s, 3H N—CH$_3$), 2.9 (s, 3H N—CH$_3$).

Example 28

3-[4-(4-Fluorophenyl)-1-methyl-5-pyridin-4-yl-1H-imidazol-2-ylsulfanyl]pentane-2,4-dione $^1$H-NMR (CDCl$_3$): δ [ppm]=8.7 (d, 2H AA' 4-Pyr), 7.3 (m, 2H 4-F-Phe), 7.2 (d, 2H BB' 4-Pyr), 6.9 (m, 2H 4-F-Phe), 3.5 (s, 3H N—CH$_2$), 2.5 (s, 6[H N—CH$_3$]$_2$) enol signal not visible.

Example 29

Ethyl 2-[4-(4-fluorophenyl)-1-methyl-5-pyridin-4-yl-1H-imidazol-2-ylsulfanyl]-3-oxobutanoate $^1$H-NMR (CDCl$_3$): δ [ppm]=13.7 (s, 0.5H OH), 8.6 (d, 2H AA' 4-Pyr), 7.3 (m, 2H 4-F-Phe), 7.2 (d, 2H BB' 4-Pyr), 6.9 (m, 2H 4-F-Phe), 5.3 (s, 0.5H CH), 4.3 (m, 2H O—CH$_2$), 3.6 (s, 3H N—CH$_3$), 2.5 (s, 3H CO—CH$_3$), 1.2 (t, 3H —CH$_3$)

Example 30

Ethyl 4-[4-(4-fluorophenyl)-1-methyl-5-pyridin-4-yl-1H-imidazol-2-ylsulfanyl]-3-oxobutanoate $^1$H-NMR (CDCl$_3$): δ [ppm]=8.7 (d, 2H AA' 4-Pyr), 7.3 (m, 2H 4-F-Phe), 7.2 (d, 2H BB' 4-Pyr), 6.9 (m, 2H 4-F-Phe), 4.2 (s, 2H CO—CH$_2$), 4.1 (m, 2H O—CH$_2$), 3.6 (s, 2H CO—CH$_2$—CO), 3.5 (s, 3H N—CH$_3$), 1.2 (t, 3H —CH$_3$)

Example 31

Methyl 4-[4-(4-fluorophenyl)-1-methyl-5-pyridin-4-yl-1H-imidazol-2-ylsulfanyl]but-2-enoate $^1$H-NMR (CDCl$_3$): δ [ppm]=8.7 (d, 2H), 7.3 (m, 2H), 7.2 (d, 2H), 6.9 (m, 2H), 6.8 (d 1H), 5.9 (d 1H), 3.9 (d 2H), 3.7 (s 3H), 3.5 (s 3H)

Example 32

2-[4-(4-Fluorophenyl)-1-methyl-5-pyridin-4-yl-1H-imidazol-2-ylsulfanyl]-1-morpholin-4-ylethanone $^1$H-NMR (CDCl$_3$): δ [ppm]=8.7 (d, 2H), 7.3 (m, 2H), 7.2 (d, 2H), 6.9 (m, 2H), 4.2 (s 2H), 3.7 (m 8H), 3.6 (s 3H)

Example 33

2-[4-(4-Fluorophenyl)-1-methyl-5-pyridin-4-yl-1H-imidazol-2-ylsulfanyl]-1-piperidin-1-ylethanone $^1$H-NMR (CDCl$_3$): δ [ppm]=8.7 (d, 2H), 7.3 (m, 2H), 7.2 (d, 2H), 6.9 (m, 2H), 4.2 (s 2H), 3.6 (m 4H), 3.5 (3H), 1.6 (m 6H)

Example 34

2-[4-(4-Fluorophenyl)-1-methyl-5-pyridin-4-yl-1H-imidazol-2-ylsulfanyl]-1-(4-hydroxypiperidin-1-yl)ethanone $^1$H-NMR (CDCl$_3$): δ [ppm]=8.7 (d, 2H), 7.3 (m, 2H), 7.2 (d, 2H), 6.9 (m, 2H), 4.2 (s 2H), 3.9 (m 4H), 3.5 (s 3H), 1.9 (m 1H), 1.6 (s 1H), 1.5 (m 4H)

Example 35

Ethyl 3-[4-(4-fluorophenyl)-1-methyl-5-pyridin-4-yl-1H-imidazol-2-ylsulfanyl]propionate $^1$H-NMR (CDCl$_3$): δ [ppm]=8.7 (d, 2H), 7.3 (m, 2H), 7.2 (d, 2H), 6.9 (m, 2H), 4.1 (q 2H), 3.5 (s 3H), 3.4 (t 2H), 2.2 (t 2H), 1.3 (t 3H)

Example 36

2-[4-(4-Fluorophenyl)-1-methyl-5-pyridin-4-yl-1H-imidazol-2-ylsulfanyl]acetic acid $^1$H-NMR (CDCl$_3$): δ [ppm]=8.7 (d, 2H), 7.4 (m, 2H), 7.3 (d, 2H), 7.0 (m, 2H), 4.0 (s 2H), 3.4 (s 3H) OH not visible

Example 37

3-[4-(4-Fluorophenyl)-1-methyl-5-pyridin-4-yl-1H-imidazol-2-ylsulfanyl]propionic acid $^1$H-NMR (CDCl$_3$): δ [ppm]=8.7 (d, 2H), 7.4 (m, 2H), 7.3 (d, 2H), 7.0 (m, 2H), 3.4 (s 3H), 3.3 (t 2H), 2.7 (t 2H) OH not visible

Example 38

1-[4-(4-Fluorophenyl)-1-methyl-5-pyridin-4-yl-1H-imidazol-2-ylsulfanyl]pentane-2,4-dione $^1$H-NMR (CDCl$_3$): δ [ppm]=8.7 (d, 2H), 7.3 (m, 2H), 7.2 (d, 2H), 6.9 (m, 2H), 5.7 (s 1H), 3.9 (2 2H), 3.5 (s 3H), 2.2 (s 2H), 2.0 (s 3H)

Example 39

4-[4-(4-Fluorophenyl)-1-methyl-5-pyridin-4-yl-1H-imidazol-2-ylsulfanyl]butanoic acid $^1$H-NMR (CDCl$_3$): δ [ppm]=8.7 (d, 2H), 7.3 (m, 2H), 7.2 (d, 2H), 6.9 (m, 2H), 3.5 (s 3H), 3.3 (t 2H), 2.6 (t 2H), 2.1 (m 2H)

Example 40

2-[4-(4-Fluorophenyl)-1-methyl-5-pyridin-4-yl-1H-imidazol-2-ylsulfanyl]-N-(2-hydroxy-1,1-bishydroxymethylethyl)acetamide $^1$H-NMR (CDCl$_3$): δ [ppm]=8.7 (d, 2H), 7.2 (m, 2H), 7.1 (d, 2H), 6.9 (m, 2H), 11.3 (s 1H), 4.7 (s 2H), 3.7 (s 3H), 3.6 (m 6H), 2.1 (s 3H)

Example 41

2-[4-(4-Fluorophenyl)-1-methyl-5-pyridin-4-yl-1H-imidazol-2-ylsulfanyl]-N,N-bis(2-hydroxyethyl)acetamide $^1$H-NMR (CDCl$_3$): δ [ppm]=8.6 (d, 2H), 7.2 (m, 2H), 7.1 (d, 2H), 6.9 (m, 2H), 4.2 (s 2H), 3.7 (m 4H), 3.6 (m 4H), 3.5 (s 3H), 2.3 (s 2H)

Example 42

N-(2,3-Dihydroxypropyl)-2-[4-(4-fluorophenyl)-1-methyl-5-pyridin-4-yl-1H-imidazol-2-ylsulfanyl]acetamide $^1$H-NMR (CDCl$_3$): δ [ppm]=8.7 (d, 2H), 7.3 (m, 2H), 7.2 (d, 2H), 6.9 (m, 2H), 11.2 (s 1H), 3.8 (m 5H), 3.6 (s 3H), 3.5 (s 2H), 2.1 (s 2H)

Example 43

3-[4-(4-Fluorophenyl)-1-methyl-5-pyridin-4-yl-1H-imidazol-2-ylsulfanyl]-N-(2-hydroxy-1,1-bishydroxymethylethyl)propionamide $^1$H-NMR (CDCl$_3$): δ [ppm]=8.6 (d, 2H), 7.3 (m, 2H), 7.2 (d, 2H), 6.9 (m, 2H), 11.3 (s 1H), 3.7 (s 3H), 3.6 (m 6H), 3.4 (t 2H), 2.8 (t 2H), 2.1 (s 3H)

Example 44

3-[4-(4-Fluorophenyl)-1-methyl-5-pyridin-4-yl-1H-imidazol-2-ylsulfanyl]-N,N-bis(2-hydroxyethyl)propionamide $^1$H-NMR (CDCl$_3$): δ [ppm]=8.6 (d, 2H), 7.3 (m, 2H), 7.2 (d, 2H), 6.9 (m, 2H), 3.8 (m 4H), 3.8 (m 4H), 3.6 (m 4H), 3.5 (s 3H), 3.3 (t 2H), 2.8 (t 2H), 2.3 (S 2H)

Example 45

Ethyl 3-[4-(4-fluorophenyl)-1-methyl-5-pyridin-4-yl-1H-imidazol-2-ylsulfanyl]-2-oxopropionate $^1$H-NMR (CDCl$_3$): δ [ppm]=8.7 (d, 2H), 7.2 (m, 2H), 7.1 (d, 2H), 6.8 (m, 2H), 4.2 (q 2H), 3.8 (s 2H), 3.6 (s 3H), 1.2 (t 3H)

Example 46

4-[2-(2-Chloroethylsulfanyl)-5-(4-fluorophenyl)-3-methyl-3H-imidazol-4-yl]pyridine $^1$H-NMR (CDCl$_3$): δ [ppm]=8.7 (d, 2H), 7.4 (m, 2H), 7.2 (d, 2H), 6.9 (m, 2H), 3.9 (t 2H), 3.6 (t 2H), 3.5 (s 3H)

Example 47

4-[2-(3-Chloropropylsulfanyl)-5-(4-fluorophenyl)-3-methyl-3H-imidazol-4-yl]pyridine $^1$H-NMR (CDCl$_3$): δ [ppm]=8.7 (d, 2H), 7.3 (m, 2H), 7.2 (d, 2H), 6.9 (m, 2H), 3.7 (t 2H), 3.5 (t 2H), 3.4 (t 2H), 2.3 (m 2H)

Example 48

2-{2-[4-(4-Fluorophenyl)-1-methyl-5-pyridin-4-yl-1H-imidazol-2-ylsulfanyl]ethyl}isoindole-1,3-dione $^1$H-NMR (CDCl$_3$): δ [ppm]=8.7 (d, 2H), 8.1 (d 2H), 7.7 (m 2H), 7.4 (m, 2H), 7.2 (d, 2H), 6.9 (m, 2H), 4.0 (t 2H), 3.2 (t 2H)

Example 49

2-{3-[4-(4-Fluorophenyl)-1-methyl-5-pyridin-4-yl-1H-imidazol-2-ylsulfanyl]propyl}isoindole-1,3-dione $^1$H-NMR (CDCl$_3$): δ [ppm]=8.7 (d, 2H), 8.1 (d 2H), 7.7 (m 2H), 7.4 (m, 2H), 7.2 (d, 2H), 6.9 (m, 2H), 3.6 (t 2H), 2.9 (t 2H), 2.0 (m 2H)

Example 50

4-[4-(4-Fluorophenyl)-1-methyl-5-pyridin-4-yl-1H-imidazol-2-ylsulfanyl]-N,N-dimethyl-3-oxobutanamide $^1$H-NMR (CDCl$_3$): δ [ppm]=8.7 (d, 2H), 7.3 (m, 2H), 7.2 (d, 2H), 6.9 (m, 2H), 5.9 (s 1H), 3.5 (s 3H), 3.2 (s 3H), 3.0 (s 3H), 2.4 (s 3H)

Example 51

7-[4-(4-Fluorophenyl)-1-methyl-5-pyridin-4-yl-1H-imidazol-2-ylsulfanyl]heptane-2,4-dione IR (ATR) 2924, 1702, 1600, 1509, 1371, 1310, 1268, 1219, 1156, 1093, 1011, 964, 836, 815, 732, 698 cm$^{-1}$ $^1$H-NMR (CDCl$_3$): δ (ppm) 8.7 (d, 2H, AA' 4-Pyr), 7.5-7.4 (m, 2H, 4-F-Phe), 7.3 (d, 2H, BB' 4-Pyr), 7.0-6.9 (m, 2H, 4-F-Phe), 5.2 (s, 2H, CO—CH$_2$—CO), 3.6 (s, 3H, N—CH$_3$), 2.6 (s, 2H, S—CH$_2$), 2.3-2.1 (m, 4H, —CH$_2$—CH$_2$—CO), 1.4 (s, 3H, CO—CH$_3$)

Example 52

2-{3-[4-(4-Fluorophenyl)-1-methyl-5-pyridin-4-yl-1H-imidazol-2-ylsulfanyl]methyl}isoindole-1,3-dione IR (ATR) 3008, 2952, 1772, 1714, 1600, 1511, 1412, 1382, 1306, 1264, 1215, 1156, 1079, 992, 967, 920, 834, 721, 673 cm$^{-1}$ $^1$H-NMR (CDCl$_3$) δ (ppm) 8.7 (d, 2H, AA' 4-Pyr), 8.1 (d, 2H, AA' Ar), 7.7 (d, 2H, BB' Ar), 7.3 (m, 2H, 4-F-Phe), 7.2 (d, 2H, BB' 4-Pyr), 6.9 (m, 2H, 4-F-Phe), 5.2 (s, 2H, S—CH$_2$)

Example 53

4-[2-Chloromethylsulfanyl-5-(4-fluorophenyl)-3-methyl-3H-imidazol-4-yl]pyridine

IR (ATR) 3008, 2937, 1604, 1482, 1370, 1296, 1225, 1160, 1130, 1099, 866, 831, 814, 708, 657 cm$^{-1}$ $^1$H-NMR (CDCl$_3$) δ (ppm) 8.7 (d, 2H, AA' 4-Pyr), 8.1 (d, 2H, AA' Ar), 7.7 (d, 2H, BB' Ar), 7.4-7.3 (m, 2H, 4-F-Phe), 7.2 (d, 2H, BB' 4-Pyr), 7.0-6.9 (m, 2H, 4-F-Phe), 5.2 (s, 2H, S—CH$_2$), 3.6 (s, 3H, N—CH$_3$)

Example 54

-Ethyl-3-{2-[4-(4-fluorophenyl)-1-methyl-5-pyridin-4-yl-1H-imidazol-2-ylsulfanyl]acetyl}urea IR (ATR) 3298, 3150, 2987, 1687, 1602, 1537, 1508, 1295, 1150, 1090, 964, 836, 735, 695 cm$^{-1}$ $^1$H-NMR (CDCl$_3$) δ (ppm) 11.3 (s, 1H, CO—NH—CO), 8.7 (d, 2H, AA' 4-Pyr), 8.1 (s, 1H, NH—C), 7.5-7.4 (m, 2H, 4-F-Phe), 7.2 (d, 2H, BB' 4-Pyr), 7.0-6.9 (m, 2H, 4-F-Phe), 3.8 (s, 2H, S—CH$_2$), 3.4 (s, 3H, N—CH$_3$), 3.3 (m, 2H, N—CH$_2$—), 1.2 (t, 3H, —CH$_3$ 7 Hz)

Example 55

4-[4-(4-Fluorophenyl)-1-methyl-5-pyridin-4-yl-1H-imidazol-2-yl-sulfanylmethyl]oxazolidin-2-one IR (ATR) 3241, 3146, 1743, 1602, 1509, 1456, 1406, 1375, 1239, 1215, 1129, 1078, 1013, 964, 843, 829, 707, 658 cm$^{-1}$ $^1$H-NMR (CDCl$_3$) δ (ppm) 8.7 (d, 2H, AA' 4-Pyr), 7.4-7.3 (m, 2H, 4-F-Phe), 7.2 (d, 2H, BB' 4-Pyr), 7.0 (m, 2H, 4-F-Phe) 5.5 (s, 1H, NH), 5.0 (m, 1H, CH), 3.8 (s, 2H, S—CH$_2$), 3.6 (t, 2H, =N—CH$_2$-7 Hz), 3.5 (s, 3H, N—CH$_3$)

Example 56

4-[4-(4-Fluorophenyl)-3-methyl-2-oxiranylmethyl-sulfanyl-1H-imidazol-4-yl]pyridine IR (ATR) 3241, 3146, 1732, 1602, 1509, 1456, 1406, 1375, 1239, 1215, 1129, 1078, 1013, 964, 843, 829, 707, 658 cm$^{-1}$ $^1$H-NMR (CDCl$_3$) δ (ppm) 8.7 (d, 2H, AA' 4-Pyr), 7.4-7.3 (m, 2H, 4-F-Phe), 7.2 (d, 2H, BB' 4-Pyr), 7.0 (m, 2H, 4-F-Phe), 5.5 (s, 1H, NH), 5.0 (m, 1H, CH), 3.8 (s, 2H, S—CH$_2$), 3.6 (t, 2H, =N—CH$_2$-7 Hz), 3.5 (s, 3H, N—CH$_3$)

Example 57

3-[4-(4-Fluorophenyl)-1-methyl-5-pyridin-4-yl-1H-imidazol-2-yl-sulfanyl]propan-1,2-diol IR (ATR) 3219, 1603, 1510, 1373, 1325, 1218, 1158, 1039, 1002, 853, 834, 713 cm$^{-1}$ $^1$H-NMR (CDCl$_3$) δ (ppm) 8.7 (d, 2H, AA' 4-Pyr), 7.4-7.3 (m, 2H, 4-F-Phe), 7.2 (d, 2H, BB' 4-Pyr), 7.0-6.9 (m, 2H, 4-F-Phe), 4.8 (s, 2H, —OH), 4.1-4.0 (m, 1H, —CH), 3.6 (m, 2H, —CH$_2$OH), 3.5 (s 3H, —CH$_3$), 3.4 (d, 2H, —CH$_2$-7 Hz)

Example 58

4-[4-(4-Fluorophenyl)-1-methyl-5-pyridin-4-yl-1H-imidazol-2-ylsulfanyl]-N,N-dimethyl-3-oxobutanamide IR (ATR) 2925, 1751, 1717, 1633, 1603, 1539, 1508, 1408, 1222, 1130, 1005, 991, 966, 872, 844, 830, 814, 735, 698 cm$^{-1}$ $^1$H-NMR (CDCl$_3$) δ (ppm) 8.7 (d, 2H, AA'4-Pyr), 7.4-7.3 (m, 2H, 4-F-Phe), 7.2 (d, 2H, BB' 4-Pyr), 7.0-6.9 (m, 2H, 4-F-Phe), 5.9 (s, 1H, —CH), 3.5 (s, 3H, =N—CH$_3$), 3.2 (s, 3H, —N—CH$_3$), 3.0 (s, 3H, —N—CH$_3$), 2.4 (s, 3H, CO—CH$_3$)

Example 59

2-[4-(4-Fluorophenyl)-1-methyl-5-pyridin-4-yl-1H-imidazol-2-ylsulfanyl]ethylamine 100 ml of HCl 10% are added to 2-{2-[4-(4-fluorophenyl)-1-methyl-5-pyridin-4-yl-1H-imidazol-2-ylsulfanyl]ethyl}isoindole-1,3-dione (2 mmol/0.917 g), and the mixture is stirred at room temperature for 6 h. The mixture is then slowly neutralized using 2N NaOH, resulting in the precipitation of 2-[4-(4-fluorophenyl)-1-methyl-5-pyridin-4-yl-1H-imidazol-2-ylsulfanyl]ethylamine as a white crystalline powder. The precipitate is filtered off with suction and washed with a little ice-cold water and dried over P$_2$O$_5$.

IR (ATR) 1599, 1508, 1450, 1407, 1370, 1326, 1212, 1157, 1049, 991, 836, 828, 709, 679 cm$^{-1}$ $^1$H-NMR (DMSO-d$_6$) δ (ppm) 8.7 (d, 2H, AA' 4-Pyr), 7.4-7.3 (m, 2H, 4-F-Phe), 7.2 (d, 2H, BB' 4-Pyr), 7.0-6.9 (m, 2H, 4-F-Phe), 3.5 (s, 3H, N—CH$_3$), 3.3 (t, 2H, S—CH$_2$ 8 Hz), 3.0 (t, 2H, N—CH$_2$ 8 Hz), 1.7 (s, 2H, —NH$_2$)

Example 60

2-[4-(4-Fluorophenyl)-1-methyl-5-pyridin-4-yl-1H-imidazol-2-ylsulfanyl]propylamine 100 ml of HCl 10% are added to 2-{3-[4-(4-fluorophenyl)-1-methyl-5-pyridin-4-yl-1H-imidazol-2-yl-sulfanyl]propyl}isoindole-1,3-dione (2 mmol/0.945 g), and the mixture is stirred at room temperature for 6 h. The mixture is then slowly neutralized using 2N NaOH, resulting in the precipitation of 2-[4-(4-fluorophenyl)-1-methyl-5-pyridin-4-yl-1H-imidazol-2-ylsulfanyl]propylamine as a white crystalline powder. The precipitate is filtered off with suction and washed with a little ice-cold water and dried over P$_2$O$_5$.

IR (ATR) 2938, 1772, 1705, 1604, 1542, 1510, 1451, 1398, 1371, 1282, 1222, 1132, 1093, 1054, 1015, 965, 877, 829, 720, 670 cm$^{-1}$ $^1$H-NMR (CDCl$_3$) δ (ppm) 8.7 (d, 2H, AA' 4-Pyr), 7.4-7.3 (m, 2H, 4-F-Phe), 7.2 (d, 2H, BB' 4-Pyr), 7.0-6.9 (m, 2H, 4-F-Phe, 3.5 (s, 3H, N—CH$_3$), 3.3 (t, 2H, S—CH$_2$ 8 Hz), 2.9 (t, 2H, N—CH$_2$ 6 Hz), 2.1 (m, 2H, —CH$_2$—), 1.6 (s, 2H, —NH$_2$)

Example 61

C-[4-(4-Fluorophenyl)-1-methyl-5-pyridin-4-yl-1H-imidazol-2-ylsulfanyl]methylamine 100 ml of HCl 10% are added to 2-{3-[4-(4-fluorophenyl)-1-methyl-5-pyridin-4-yl-1H-imidazol-2-yl-sulfanyl]methyl}isoindole-1,3-dione (2 mmol/0.889 g) and the mixture is stirred at room temperature for 6 h. The mixture is then slowly neutralized using 2N NaOH, resulting in the precipitation of C-[4-(4-fluorophenyl)-1-methyl-5-pyridin-4-yl-1H-imidazol-2-ylsulfanyl]methylamine as a white crystalline powder. The precipitate is filtered off with suction and washed with a little ice-cold water and dried over P$_2$O$_5$.

IR (ATR) 3058, 1585, 1499, 1409, 1276, 1228, 1167, 1115, 967, 842, 814, 679 cm$^{-1}$ $^1$H-NMR (CDCl$_3$) δ (ppm) 8.7 (d, 2H, AA' 4-Pyr), 7.5-7.4 (m, 2H, 4-F-Phe), 7.3 (d, 2H, BB' 4-Pyr), 7.0-6.9 (m, 2H, 4-F-Phe), 3.6 (s, 2H, S—CH$_2$), 3.5 (s, 3H, N—CH$_3$, 1.8 (s, 2H, —NH$_2$)

Example 62

1-{2-[4-(4-Fluorophenyl)-1-methyl-5-pyridin-4-yl-1H-imidazol-2-ylsulfanyl]acetyl}pyrrolidine-2-carboxylic acid 2-[4-(4-Fluorophenyl)-1-methyl-5-pyridin-4-yl-1H-imidazol-2-ylsulfanyl]acetic acid (1 mmol/0.344 g) are dissolved in 100 ml of absolute THF, carbonyldiimidazole (1 mmol/0.162 g) is added and the mixture is stirred at room temperature until the evolution of carbon dioxide has ceased. Histidine (1 mmol) is then added, and the mixture is heated under reflux for 2 h. The mixture is then poured into 400 ml of 1 N $Na_2CO_3$ solution and concentrated in a rotary evaporator. The residue is extracted 3 times with in each case 150 ml of dichloromethane/ethanol 1:1, dried over sodium sulfate and concentrated in a rotary evaporator. The residue is dissolved in a little acetone and re-precipitated using diethyl ether. The precipitate formed is filtered off with suction and dried over $P_2O_5$.

IR (ATR) 3385, 2976, 1635, 1567, 1510, 1403, 1296, 1156, 1135, 1013, 923, 837, 816 $cm^{-1}$ $^1$H-NMR ($CDCl_3$) δ (ppm) 8.7 (d, 2H, AA' 4-Pyr), 7.4-7.3 (m, 2H, 4-F-Phe), 7.2 (d, 2H, BB' 4-Pyr), 7.0-6.9 (m, 2H, 4-F-Phe), 4.0 (s, 2H, S—$CH_2$), 3.7-3.3 (m, 3H, CH—$CH_2$—), 2.2-1.8 (m, 4H, —$CH_2$—$CH_2$—N), OH not visible.

Example 63

Ethyl 3-{2-[4-(4-fluorophenyl)-1-methyl-5-pyridin-4-yl-1H-imidazol-2-ylsulfanyl]acetylamino}propionate 2-[4-(4-Fluorophenyl)-1-methyl-5-pyridin-4-yl-1H-imidazol-2-ylsulfanyl]acetic acid (2 mmol/0.688 g) is dissolved in 100 ml of absolute tetrahydrofuran (THF), carbonyldiimidazole (2 mmol/0.324 g) is added and the mixture is stirred at room temperature until the evolution of carbon dioxide has ceased. Ethyl ss-alaninate (2 mmol) is then added, and the mixture is heated under reflux for 2 h. The mixture is then poured into 400 ml of 1 N $Na_2CO_3$ solution and concentrated in a rotary evaporator. The residue is extracted 3 times with in each case 150 ml of dichloromethane/ethanol 1:1, dried over sodium sulfate and concentrated in a rotary evaporator. The residue is dissolved in a little acetone and re-precipitated using diethyl ether. The precipitate formed is filtered off with suction and dried over $P_2O_5$.

IR (ATR) 3281, 3061, 2983, 1728, 1660, 1601, 1540, 1510, 1408, 1373, 1314, 1219, 1183, 1157, 965, 837, 761, 698 $cm^{-1}$ $^1$H-NMR ($CDCl_3$) δ (ppm) 8.4 (s, 1H, NH), 7.4-7.3 (m, 2H, 4-F-Phe), 7.2 (d, 2H, BB' 4-Pyr), 7.0-6.9 (m, 2H, 4-F-Phe), 4.2-4.1 (m, 2H, O—$CH_2$), 3.8 (s, 2H, S—$CH_2$ 8 Hz), 3.6 (q, 2H, N—$CH_2$ 6 Hz), 3.5 (s, 3H, N—$CH_3$), 2.3 (t, 2H, CO—$CH_2$ 7 Hz), 1.1 (t, 3H, —$CH_3$ 7 Hz)

Example 64

Dimethyl 2-{2-[4-(4-fluorophenyl)-1-methyl-5-pyridin-4-yl-1H-imidazol-2-ylsulfanyl]acetylamino}pentanedioate 2-[4-(4-Fluorophenyl)-1-methyl-5-pyridin-4-yl-1H-imidazol-2-ylsulfanyl]acetic acid (2 mmol/0.688 g) is dissolved in 100 ml of absolute THF, carbonyldiimidazole (2 mmol/0.324 g) is added and the mixture is stirred at room temperature until the evolution of carbon dioxide has ceased. Dimethyl glutaminate (2 mmol) is then added, and the mixture is heated under reflux for 2 h. The mixture is then poured into 400 ml of 1 N $Na_2CO_3$ solution and concentrated in a rotary evaporator. The residue is extracted 3 times with in each case 150 ml of dichloromethane/ethanol 1:1, dried over sodium sulfate and concentrated in a rotary evaporator. The residue is dissolved in a little acetone and re-precipitated using diethyl ether. The precipitate formed is filtered off with suction and dried over $P_2O_5$.

IR (ATR) 3278, 3061, 2953, 1734, 1664, 1603, 1552, 1509, 1435, 1409, 1350, 1265, 1213, 1157, 1072, 985, 845, 679 $cm^{-1}$ $^1$H-NMR ($CDCl_3$) δ (ppm) 8.9 (s, 1H, NH), 8.7 (d, 2H, AA' 4-Pyr), 7.4-7.3 (m, 2H, 4-F-Phe), 7.2 (d, 2H, BB' 4-Pyr), 7.0-6.9 (m, 2H, 4-F-Phe), 4.6 (q 1H, —CH 6 Hz), 3.8 (s, 2H, S—$CH_2$), 3.6 (s, 3H, O—$CH_3$), 3.5 (s, 3H, O—$CH_3$), 3.4 (s, 3H, N—$CH_3$), 2.4-2.1 (m, 4H, —$CH_2$—$CH_2$—)

Example 65

1-Hydrogen 5-methyl 2-{2-[4-(4-fluorophenyl)-1-methyl-5-pyridin-4-yl-1H-imidazol-2-ylsulfanyl]acetylamino}pentanediotate 100 ml of HCl 10% are added to dimethyl 2-{2-[4-(4-fluorophenyl)-1-methyl-5-pyridin-4-yl-1H-imidazol-2-ylsulfanyl]acetylamino}pentanedioate (0.8 mmol/0.400 g) and the mixture is stirred at room temperature for 6 h. The mixture is then slowly neutralized using 2N NaOH, resulting in the precipitation of 1-hydrogen 5-methyl 2-{2-[4-(4-fluorophenyl)-1-methyl-5-pyridin-4-yl-1H-imidazol-2-ylsulfanyl]acetylamino}pentanedioate as a yellowish crystalline powder. The precipitate is filtered off with suction and washed with a little ice-cold water and dried over $P_2O_5$.

IR (ATR) 2924, 2370, 2356, 2342, 1727, 1660, 1604, 1512, 1409, 1371, 1218, 1012, 837, 816, 667 $cm^{-1}$ $^1$H-NMR (DMSO-$d_6$) δ (ppm) 8.7 (d, 2H, AA' 4-Pyr), 8.3 (s, 1H, NH), 7.4-7.3 (m, 2H, 4-F-Phe), 7.2 (d, 2H, BB' 4-Pyr), 7.0-6.9 (m, 2H, 4-F-Phe), 4.5 (q, 1H, CH 6 Hz), 3.9 (s, 2H, S—$CH_2$), 3.6 (s, 3H, O—$CH_3$), 3.5 (s, 3H, N—$CH_3$), 2.3-1.9 (m, 4H, —$CH_2$—$CH_2$—), OH not visible

Example 66

3-{2-[4-(4-Fluorophenyl)-1-methyl-5-pyridin-4-yl-1H-imidazol-2-ylsulfanyl]acetamino}propionic acid 100 ml of HCl 10% are added to ethyl 3-{2-[4-(4-fluorophenyl)-1-methyl-5-pyridin-4-yl-1H-imidazol-2-ylsulfanyl]acetylamino}propionate) (2 mmol/0.855 g) and the mixture is stirred at room temperature for 6 h. The mixture is then slowly neutralized using 2N NaOH, resulting in the precipitation of 3-{2-[4-(4-fluorophenyl)-1-methyl-5-pyridin-4-yl-1H-imidazol-2-ylsulfanyl]acetamino}propionic acid as a yellowish-white powder. The precipitate is filtered off with suction and washed with a little ice-cold water and dried over $P_2O_5$.

IR (ATR) 3061, 2952, 1928, 1711, 1602, 1511, 1408, 1371, 1219, 1157, 1052, 1010, 965, 836, 815, 761, 699 $cm^{-1}$ $^1$H-NMR ($CDCl_3$) δ (ppm) 9.2 (s, 1H, OH), 8.6 (d, 2H, AA' 4-Pyr), 8.3 (s, 1H, NH), 7.4-7.3 (m, 2H, 4-F-Phe), 7.2 (d, 2H, BB' 4-Pyr), 7.0-6.9 (m, 2H, 4-F-Phe), 3.8 (s, 2H, S—$CH_2$), 3.7-3.6 (m, 2H, N—$CH_2$—), 3.5 (s, 3H, N—$CH_3$), 2.5 (t, 2H, $CH_2$—CO 7 Hz)

Example 67

N-{4-[2-(2,3-dihydroxypropanesulfanyl)-5-(4-fluorophenyl)-3-methyl-3H-imidazol-4-yl]pyridin-2-yl}acetamide $K_2CO_3$ (3.1 mmol/0.34 g) is added to undissolved N-{4-[5-(4-fluorophenyl)-3-methyl-2-thioxo-2H-imidazol-4-yl]pyridin-2-yl}acetamide (prepared according to J. Org. Chem. 1967, 32, 1562-1565 and Helv. Chim. Acta 1998, 81, 1585-1595) (2.9 mmol/1.0 g), and the mixture is then suspended in 100 ml of absolute acetone. 1-bromopropane-2,3-diol (2.9 mmol/0.452 g) is then added, and the mixture is stirred at room temperature for 24 h. The mixture is then heated under reflux for 3 h, the precipitate is filtered off and the filtrate is concentrated under reduced pressure using a rotary evaporator. The oily residue is separated on a column (mobile phase: $CH_2Cl_2$/EtOH, 9.5:0.5).

IR (ATR) 3209, 1698, 1612, 1552, 1506, 1455, 1416, 1262, 1219, 1137, 1089, 1075, 1029, 890, 837, 711, 669 $cm^{-1}$ $^1$H-NMR (CDCl$_3$) δ (ppm) 8.7 (s, 1H, NH), 8.3 (d, 1H, 4-F-Phe), 8.2 (d, 1H, 4-Pyr), 7.3-7.2 (m, 2H, 4-F-Phe), 7.0-6.9 (m, 2H, 4-F-Phe), 6.8 (d, 1H, 4-Pyr), 3.9 (t 2H, S—CH$_2$ 8 Hz), 3.6 (t, 2H, CH$_2$—OH 7 Hz), 3.6 (s, 3H, N—CH$_3$), 3.3 (m, 1H, CH—OH), 2.1 (s, 3H, CO—CH$_3$) OH not visible.

Example 68

3-[5-(2-Aminopyridin-4-yl)-4-(4-fluorophenyl)-1-methyl-1H-imidazol-2-ylsulfanyl]propane-1,2-diol 50 ml of HCl 10% are added to N-{4-[2-(2,3-dihydroxypropanesulfanyl)-5-(4-fluorophenyl)-3-methyl-3H-imidazol-4-yl]pyridin-2-yl}acetamide (obtained according to example 67) (6 mmol/0.25 g), and the mixture is stirred at room temperature for 6 h. The mixture is then slowly neutralized using 2N NaOH, resulting in the precipitation of 3-[5-(2-aminopyridin-4-yl)-4-(4-fluorophenyl)-1-methyl-1H-imidazol-2-ylsulfanyl]propane-1,2-diol as a yellowish powder. The precipitate is filtered off with suction, washed with a little ice cold water and dried over $P_2O_5$.

IR (ATR) 3172, 2373, 2317, 1643, 1428, 1347, 1069, 880, 863, 846, 667, 685 $cm^{-1}$ $^1$H-NMR (CDCl$_3$) δ (ppm) 8.1 (d, 1H, 4-Pyr), 7.4-73 (m, 2H, 4-F-Phe), 6.9 (t, 2H, 4-F-Phe), 6.5 (d 1H, 4-Pyr), 6.3 (s 1H, 4-Pyr), 4.6 s 2H, NH2), 4.0 (t, 2H, CH2—OH 6 Hz), 3.7-3.6 (m, 1H, CH—OH), 3.4 (s, 3H, N—CH$_3$), 3.3 (d, 2H, S—CH$_2$ 7 Hz), 2.0 (s, 2H, OH)

Example 69

2-[5-(2-Acetylaminopyridin-4-yl)-4-(4-fluorophenyl)-1-methyl-1H-imidazol-2-ylsulfanyl]-N,N-bis(2-hydroxyethyl)acetamide $K_2CO_3$ (3.1 mmol/0.34 g) is added to undissolved N-{4-[5-(4-fluorophenyl)-3-methyl-2-thioxo-2H-imidazol-4-yl]pyridin-2-yl}acetamide (2.23 mmol/0.8 g), and the mixture is then suspended in 100 ml of absolute acetone. 2-Chloro-N,N-bis(2-hydroxyethyl)acetamide (2.3 mmol/0.455 g) is then added, and the mixture is stirred at room temperature for 24 h. The mixture is then heated under reflux for 3 h, the precipitate is filtered off and the filtrate is concentrated under reduced pressure using a rotary evaporator. The oily residue is separated on a column (mobile phase: $CH_2Cl_2$/EtOH, 9.5:0.5).

IR (ATR) 2926, 1677, 1607, 1542, 1504, 1410, 1264, 1218, 1157, 1096, 1017, 888, 839, 816, 743, 689 $cm^{-1}$ $^1$H-NMR (CDCl$_3$) δ (ppm) 8.3 (d, 2H, 4-Pyr), 8.2 (s, 1H, 4-Pyr), 7.4-7.3 (m, 2H, 4-F-Phe), 7.0-6.9 (m, 2H, 4-F-Phe), 4.2 (S, 2H, s-CH$_3$), 3.9-3.8 (m, 6H, —CH$_2$—), 3.6 (s, 3H, N—CH$_3$), 2.2 (s, 3H, CO—CH$_3$), 1.7 (s, 2H, —OH)

Example 70

Ethyl 3-[5-(2-acetylaminopyridin-4-yl)-4-(4-fluorophenyl)-1-methyl-1H-imidazol-2-ylsulfanyl]propionate $K_2CO_3$ (3.1 mmol/0.34 g) is added to undissolved N-{4-[5-(4-fluorophenyl)-3-methyl-2-thioxo-2H-imidazol-4-yl]pyridin-2-yl}acetamide (2.23 mmol/0.8 g), and the mixture is then suspended in 100 ml of absolute acetone. Ethyl 3-bromopropionate (2.3 mmol/0.422 g) are then added, and the mixture is stirred at room temperature for 24 h. The mixture is then heated under reflux for 3 h, the precipitate is filtered off and the filtrate is concentrated under reduced pressure using a rotary evaporator. The oily residue is separated on a column (mobile phase: $CH_2Cl_2$/EtOH, 9.5:0.5).

IR (ATR) 3265, 1731, 1665, 1607, 1543, 1503, 1420, 1241, 1178, 1019, 968, 844, 760, 678 $cm^{-1}$ $^1$H-NMR (CDCl$_3$) δ (ppm) 8.6 (s, 1H, NH), 8.2 (d, 2H, 4-Pyr), 7.4-7.3 (m, 2H, 4-F-Phe), 7.0-6.9 (m, 3H, 4-Pyr, 4-F-Phe), 4.1 (d, 2H, O—CH$_2$ 6 Hz), 3.5 (s, 3H, N—CH$_3$), 3.4 (t, 2H, S—CH$_2$ 8 Hz), 2.9 (t, 2H, CH$_2$—CO 6 Hz), 2.2 (s, 3H, CO—CH$_3$), 1.2 (t, 3H, —CH$_3$ 7 Hz)

Example 71

2-[5-(2-Aminopyridin-4-yl)-4-(4-fluorophenyl)-1-methyl-1H-imidazol-2-ylsulfanyl]-N,N-bis(2-hydroxyethyl)acetamide 50 ml of HCl 10% are added to 2-[5-(2-acetylaminopyridin-4-yl)-4-(4-fluorophenyl)-1-methyl-1H-imidazol-2-ylsulfanyl]-N,N-bis(2-hydroxyethyl)acetamide (0.6 mmol/0.293 g), and the mixture is stirred at room temperature for 6 h. The mixture is then slowly neutralized using 2N NaOH, resulting in the precipitation of 2-[5-(2-aminopyridin-4-yl)-4-(4-fluorophenyl)-1-methyl-1H-imidazol-2-ylsulfanyl]-N,N-bis(2-hydroxyethyl)acetamide as a whitish powder. The precipitate is filtered off with suction, washed with a little ice-cold water and dried over $P_2O_5$.

IR (ATR) 3337, 1619, 1542, 1509, 1442, 1219, 1022, 867, 840 $cm^{-1}$ $^1$H-NMR (CDCl$_3$) δ (ppm) 8.2 (d 2H, 4-Pyr), 7.4-7.3 (m, 2H, 4-F-Phe), 7.0-6.9 (m, 3H, 4-Pyr, 4-F-Phe), 4.5 (s, 2H, —NH$_2$), 4.2-3.8 (m, 4H, CH$_2$—OH), 3.5 (s, 3H, N—CH$_3$), 2.6-1.9 (m, 4H, N—CH$_2$—), 1.6 (s, 2H, —OH)

Example 72

3-[5-(2-Aminopyridin-4-yl)-4-(4-fluorophenyl)-1-methyl-1H-imidazol-2-ylsulfanyl]propionic acid 50 ml of HCl 10% are added to ethyl 3-[5-(2-acetylaminopyridin-4-yl)-4-(4-fluorophenyl)-1-methyl-1H-imidazol-2-ylsulfanyl]propionate (0.67 mmol/0.297 g), and the mixture is stirred at room temperature for 6 h. The mixture is then slowly neutralized using 2N NaOH, resulting in the precipitation of 3-[5-(2-aminopyridin-4-yl)-4-(4-fluorophenyl)-1-methyl-1H-imidazol-2-ylsulfanyl]propionic acid as a whitish powder. The precipitate is filtered off with suction, washed with a little ice-cold water and dried over $P_2O_5$.

IR (ATR) 3207, 1626, 1567, 1539, 1508, 1397, 1301, 1212, 1159, 1133, 997, 977, 893, 843, 807 cm$^{-1}$ $^1$H-NMR (CDCl$_3$) δ (ppm) 8.0 (d, 1H, 4-Pyr), 7.4-7.3 (m, 2H, 4-F-Phe), 7.0-6.9 (m, 2H, 4-F-Phe), 6.6-6.5 (m, 2H, 4-Pyr), 4.2 (s, 2H, NH$_2$), 3.6 (s, 3H, N—CH$_3$), 3.3 (t, 2H, S—CH$_2$ 8 Hz), 2.6 (m, 2H, CH$_2$—CO)

We claim:

1. A 2-thio-substituted imidazole derivative of the formula I

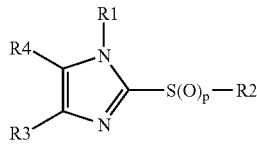

in which

R$^1$ is H or C$_1$-C$_6$-alkyl;

R$^2$ is selected from the group consisting of:
a) C$_1$-C$_6$-alkyl which is substituted by 2 or 3 hydroxyl groups, halogen atoms, NR$^5$R$^6$ or C$_1$-C$_4$-alkoxy groups, where R$^5$ is H, C$_1$-C$_6$-alkyl, phenyl-C$_1$-C$_4$-alkyl or phenyl and R$^6$ is H or C$_1$-C$_6$-alkyl,
b) C$_1$-C$_6$-alkyl which is substituted by 1, 2 or 3 radicals of the formula —COOR$^5$, where R$^5$ is H, C$_1$-C$_6$-alkyl, phenyl-C$_1$-C$_4$-alkyl or phenyl,
c) C$_1$-C$_6$-alkyl which is substituted by at least one radical of the formula —COOR$^5$ and at least one hydroxyl group, where R$^5$ is H, C$_1$-C$_6$-alkyl, phenyl-C$_1$-C$_4$-alkyl or phenyl,
d) a radical of the formula II

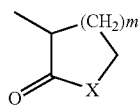

in which X is O or NR$^6$, m is 1 or 2 and R$^6$ is H or C$_1$-C$_6$-alkyl,
e) a radical of the formula

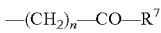
—(CH$_2$)$_n$—CO—R$^7$ in which R$^7$ is C$_1$-C$_3$-alkyl, phenyl, benzyl or phenethyl and n is 1, 2 or 3,
f) a radical of the formula

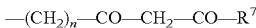
—(CH$_2$)$_n$—CO—CH$_2$—CO—R$^7$ in which R$^7$ is C$_1$-C$_3$-alkyl, phenyl, benzyl or phenethyl and n is 1, 2 or 3,
g) a radical of the formula

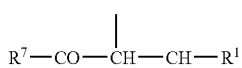
R$^7$—CO—CH—CH—R$^1$ in which the radicals R$^7$, which are identical or different, are C$_1$-C$_3$-alkyl, phenyl, benzyl or phenethyl,
h) a radical of the formulae

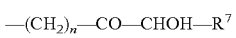
—(CH$_2$)$_n$—CO—CHOH—R$^7$

—(CH$_2$)$_n$—CHOH—CO—R$^7$

—(CH$_2$)$_n$—CO—CH$_2$—CHOH—R$^7$

—(CH$_2$)$_n$—CHOH—CH$_2$—CO—R$^7$ in which R$^7$ is C$_1$-C$_3$-alkyl, phenyl, benzyl or phenethyl and n is 1, 2 or 3,
i) a radical of the formulae

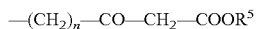
—(CH$_2$)$_n$—CO—CH$_2$—COOR$^5$

—CH(COR$^7$)—COOR$^5$

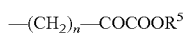
—(CH$_2$)$_n$—COCOOR$^5$ in which R$^5$ is H, C$_1$-C$_6$-alkyl, phenyl-C$_1$-C$_4$-alkyl or phenyl, R$^7$ is C$_1$-C$_3$-lkyl, phenyl, benzyl or phenethyl and n is 1, 2 or 3,
j) a radical of the formula

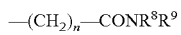
—(CH$_2$)$_n$—CONR$^8$R$^9$ in which R$^8$ and R$^9$, which may be identical or different, are H, C$_1$-C$_6$-alkyl, C$_1$-C$_6$-alkyl, C$_1$-C$_6$-alkyl which is substituted by one, two or three hydroxyl groups, C$_1$-C$_6$-alkyl which is substituted by a COOH group, phenyl or benzyl, or R$^8$ and R$^9$ together with the nitrogen atom to which they are attached are a saturated heterocycle which has 5 or 6 ring atoms and one or two heteroatoms independently of one another selected from the group consisting of N, O and S and which may be substituted by one or two groups independently of one another selected from the group consisting of C$_1$-C$_6$-alkyl and hydroxyl, and n is 1, 2 or 3,
k) a radical of the formula —(CH$_2$)$_n$CONR$^{10}$—CONR$^8$R$^9$
in which R$^8$ and R$^9$, which may be identical or different, are H, C$_1$-C$_6$-alkyl, C$_1$-C$_6$-alkyl which is substituted by one or two hydroxyl groups, C$_1$-C$_6$-alkyl which is substituted by a COOH group, phenyl or benzyl or R$^8$ and R$^9$ together with the nitrogen atom to which they are attached are saturated heterocycle which has 5 or 6 ring atoms and one or two heteroatoms independently of one another selected from the group consisting of N, O, and S, and n is 1, 2 or 3 and R$^{10}$ is H or C$_1$-C$_6$-alkyl,
l) C$_2$-C$_6$-alkenyl which is substituted by one or two groups of the formula —COOR$^5$, where R$^5$ is H, C$_1$-C$_6$-alkyl, phenyl or benzyl,
m) C$_1$-C$_6$-alkyl which is substituted by a non-aromatic 3- to 6-memberedn heterocyclic radical which has one or two heteroatoms independently of one another selected from the group consisting of N and O, p is 0, 1 or 2;

one of the radicals R$^3$ and R$^4$ represents 4-pyridyl, which may have 1 or 2 substituents independently of one another selected from the group consisting of amino, C$_1$-C$_4$-alkylamino, di-C$_1$-C$_4$-alkylamino, phenyl-C$_1$-C$_4$-alkylamino and —NR$^{12}$COR$^{11}$, where R$^{11}$ is C$_1$-C$_4$-alkyl, phenyl which may have one or two substituents independently of one another selected from the group consisting of C$_1$-C$_4$-alkyl, C$_1$-C$_4$-alkoxy and halogen, and R$^{12}$ is H, C$_1$-C$_4$-alkyl or benzyl, and the second of the radicals R$^3$ and R$^4$ is aryl, or an optical isomer or physiologically acceptable salt thereof.

2. A compound as claimed in claim 1, characterized in that R$^2$ is a C$_1$-C$_6$-alkyl group which is substituted by 2 hydroxyl groups, 1 or 2 —COOR$^5$ groups or one hydroxyl group and one —COOR$^5$ group, where R$^5$ is H or C$_1$-C$_6$-alkyl.

3. A compound as claimed in claim 1, characterized in that R$^2$ is one of the radicals listed in claim 1 under g), h) or j).

4. A compound as claimed in claim 1, characterized in that $R^2$ is a radical of the formula —$(CH_2)_n CONR^8R^9$ where n, $R^8$ and $R^9$ are as defined in claim 1.

5. A compound as claimed in claim 4, characterized in that $R^8$ is H and $R^9$ is $C_1$-$C_6$-alkyl which is substituted by 1, 2 or 3 hydroxyl groups.

6. A compound as claimed in claim 4, characterized in that $R^8$ and $R^9$ are $C_1$-$C_6$-alkyl which is substituted by 1, 2 or 3 hydroxyl groups.

7. A compound as claimed in claim 1, characterized in that one of the radicals $R^3$ and $R^4$ is halogen-substituted phenyl.

8. A compound as claimed in claim 7, characterized in that one of the radicals $R^3$ and $R^4$ is 4-fluorophenyl.

9. A compound as claimed in claim 1, characterized in that $R^4$ is 4-pyridyl which is substituted by amino, $C_1$-$C_4$-alkylamino or —$NR^{12}COR^{11}$, where $R^{11}$ and $R^{12}$ are as defined in claim 1.

10. A compound as claimed in claim 9, characterized in that $R^4$ is 4-pyridyl which is substituted by phenyl-$C_1$-$C_4$-alkylamino.

11. A compound as claimed in claim 9, characterized in that $R^4$ is 4-pyridyl which is substituted by —$NR^{12}COR^{11}$, where $R^{11}$ is $C_1$-$C_6$-alkyl and $R^{12}$ is H or $C_1$-$C_6$-alkyl.

12. A compound as claimed in claim 1, characterized in that the substituent of the 4-pyridyl group is located in the 2-position.

13. A pharmaceutical composition, comprising at least one compound as claimed in claim 1, if appropriate together with one pr more pharmaceutically acceptable carriers and/or additives.

14. The compound of claim 1 wherein the second of radicals $R^3$ and $R^4$ is aryl, and is substituted by a halogen atom.

* * * * *